(12) United States Patent
Mistry

(10) Patent No.: US 9,074,189 B2
(45) Date of Patent: *Jul. 7, 2015

(54) CELLULAR THERAPY FOR OCULAR DEGENERATION

(75) Inventor: Sanjay Mistry, Downingtown, PA (US)

(73) Assignee: Janssen Biotech, Inc., Horsham, PA (US)

( * ) Notice: Subject to any disclaimer, the term of this patent is extended or adjusted under 35 U.S.C. 154(b) by 530 days.

This patent is subject to a terminal disclaimer.

(21) Appl. No.: 11/446,462

(22) Filed: Jun. 2, 2006

(65) Prior Publication Data

US 2006/0280729 A1    Dec. 14, 2006

Related U.S. Application Data

(60) Provisional application No. 60/688,637, filed on Jun. 8, 2005.

(51) Int. Cl.
| | | |
|---|---|---|
| A61K 48/00 | (2006.01) | |
| A01N 63/00 | (2006.01) | |
| C12N 5/0789 | (2010.01) | |
| C12N 5/0775 | (2010.01) | |
| C12N 5/077 | (2010.01) | |
| C12N 5/073 | (2010.01) | |
| A61K 35/12 | (2015.01) | |

(52) U.S. Cl.
CPC ......... *C12N 5/0663* (2013.01); *A61K 2035/124* (2013.01); *C12N 5/0605* (2013.01); *C12N 5/0668* (2013.01)

(58) Field of Classification Search
CPC . A61K 35/28; A61K 2035/124; A61K 35/50; A61K 2300/00; A61K 35/545; C12N 5/0607; C12N 5/0606; C12N 5/0603; C12N 5/0663; C12N 5/0623; C12N 5/0621; C12N 5/0647; C12N 5/0634; C12N 2502/1358; C12N 2502/21; G01N 33/5073

See application file for complete search history.

(56) References Cited

U.S. PATENT DOCUMENTS

| | | |
|---|---|---|
| 3,209,652 A | 10/1965 | Burgsmueller |
| 3,845,641 A | 11/1974 | Waller |
| 3,935,067 A | 1/1976 | Thayer |
| 4,499,802 A | 2/1985 | Simpson |
| 4,537,773 A | 8/1985 | Shenvi |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,686,090 A | 11/1997 | Schilder et al. |
| 5,713,957 A | 2/1998 | Steele et al. |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,780,454 A | 7/1998 | Adams et al. |
| 5,834,308 A | 11/1998 | Peck et al. |
| 5,843,780 A | 12/1998 | Thomson |
| 5,908,782 A | 6/1999 | Marshak et al. |
| 5,914,262 A | 6/1999 | MacMichael et al. |
| 5,942,435 A | 8/1999 | Wheeler |
| 6,001,647 A | 12/1999 | Peck et al. |
| 6,022,743 A | 2/2000 | Naughton et al. |
| 6,083,903 A | 7/2000 | Adams et al. |
| 6,087,113 A | 7/2000 | Caplan et al. |
| 6,200,806 B1 | 3/2001 | Thomson |
| 6,261,549 B1 | 7/2001 | Fernandez et al. |
| 6,281,012 B1 | 8/2001 | McIntosh et al. |
| 6,297,217 B1 | 10/2001 | Adams et al. |
| 6,306,424 B1 | 10/2001 | Vyakarnan et al. |
| 6,328,960 B1 | 12/2001 | McIntosh et al. |
| 6,331,298 B1 | 12/2001 | Ferguson et al. |
| 6,333,029 B1 | 12/2001 | Vyakarnam et al. |
| 6,365,149 B2 | 4/2002 | Vyakarnam et al. |
| 6,436,704 B1 | 8/2002 | Roberts et al. |
| 6,458,589 B1 | 10/2002 | Rambhatla |
| 6,458,593 B1 | 10/2002 | Musick et al. |
| 6,509,369 B2 | 1/2003 | Scott et al. |
| 6,521,427 B1 | 2/2003 | Evans |
| 6,534,084 B1 | 3/2003 | Vyakarnam et al. |
| 6,599,323 B2 | 7/2003 | Melican et al. |
| 6,617,152 B2 | 9/2003 | Bryhan et al. |
| 6,617,317 B1 | 9/2003 | Adams et al. |
| 6,626,950 B2 | 9/2003 | Brown et al. |

(Continued)

FOREIGN PATENT DOCUMENTS

| | | |
|---|---|---|
| CN | 1389565 A | 7/2002 |
| CN | 101092606 A | 12/2007 |

(Continued)

OTHER PUBLICATIONS

Scullica et al. Documenta Ophthal. 2001. 102: 237-250.*
Chapple et al. Trends in Mol. Med. 2001. 7: 414-421.*
Lee et al. Biochem Biophys. Res. Commun. 2004, 320: 273-278.*
Chacko, David M., et al., "Survival and Differentiation of Cultured Retinal Progenitors Transplanted in the Subretinal Space of the Rat", Biochemical and Biophysical Research Communication, 2000 (268): 842-846.
Doyle et al., (eds.), 1995, Cell & Tissue Culture: Laboratory Procedures, John Wiley & Sons, Chichester.
Ho and Wang (eds.), 1991, Animal Cell Bioreactors, Butterworth-Heinemann, Boston.
Enzmann, V. et al., "Enhanced Induction of RPE Lineage Markers in Pluripotent Neural Stem Cells Engrafted into the Adult Rat Subretinal Space", 2003, Investig. Ophthalmol. Visual Sci, vol. 44, No. 12, pp. 5417-5422.

(Continued)

*Primary Examiner* — Chang-Yu Wang
(74) *Attorney, Agent, or Firm* — Mark R. Warfield

(57) ABSTRACT

Compositions and methods applicable to cell-based or regenerative therapy for ophthalmic diseases and disorders comprising mesenchymal stem cells, particularly those characterized by the expression of at least one of the following surface markers: CD29, CD44, CD105 or CD166, and the lack of expression of at least one of CD14, CD34 or CD45.

8 Claims, 4 Drawing Sheets

(56) References Cited

U.S. PATENT DOCUMENTS

| | | | |
|---|---|---|---|
| 6,642,048 B2 | 11/2003 | Xu | |
| 6,656,488 B2 | 12/2003 | Yi et al. | |
| 6,670,127 B2 | 12/2003 | Evans | |
| 6,703,017 B1 | 3/2004 | Peck et al. | |
| 6,713,446 B2 | 3/2004 | Gupta | |
| 6,793,945 B2 | 9/2004 | Bathurst et al. | |
| 6,800,480 B1 | 10/2004 | Bodnar et al. | |
| 6,815,203 B1 | 11/2004 | Bonner-Weir et al. | |
| 6,958,319 B2 | 10/2005 | Gupta | |
| 6,987,110 B2 | 1/2006 | Zhang et al. | |
| 7,005,252 B1 | 2/2006 | Thomson et al. | |
| 7,033,831 B2 | 4/2006 | Fisk et al. | |
| 7,157,275 B2 | 1/2007 | Guarino et al. | |
| 7,297,539 B2 | 11/2007 | Mandalam et al. | |
| 7,326,572 B2 | 2/2008 | Fisk et al. | |
| 7,371,576 B2 | 5/2008 | Tsang et al. | |
| 7,410,798 B2 | 8/2008 | Mandalam et al. | |
| 7,413,734 B2 * | 8/2008 | Mistry et al. | 424/93.7 |
| 7,442,548 B2 | 10/2008 | Thomson et al. | |
| 7,449,334 B2 | 11/2008 | Thomson et al. | |
| 7,510,876 B2 | 3/2009 | D'Amour et al. | |
| 7,534,608 B2 | 5/2009 | Martinson et al. | |
| 7,569,385 B2 * | 8/2009 | Haas | 435/325 |
| 7,585,672 B2 | 9/2009 | Odorico et al. | |
| 7,704,738 B2 | 4/2010 | D'Amour et al. | |
| 7,993,920 B2 | 8/2011 | Martinson et al. | |
| 8,187,878 B2 | 5/2012 | Dalton et al. | |
| 2002/0072117 A1 | 6/2002 | Xu | |
| 2003/0082155 A1 | 5/2003 | Habener | |
| 2003/0138948 A1 | 7/2003 | Fisk et al. | |
| 2003/0180903 A1 | 9/2003 | Bryhan et al. | |
| 2004/0015805 A1 | 1/2004 | Kidd | |
| 2004/0058412 A1 | 3/2004 | Ho et al. | |
| 2004/0062753 A1 | 4/2004 | Rezania | |
| 2004/0106196 A1 | 6/2004 | Fraser et al. | |
| 2004/0121460 A1 | 6/2004 | Lumelsky et al. | |
| 2004/0121461 A1 * | 6/2004 | Honmou et al. | 435/368 |
| 2004/0132729 A1 | 7/2004 | Salituro et al. | |
| 2004/0161419 A1 | 8/2004 | Strom et al. | |
| 2004/0171623 A1 | 9/2004 | Reynolds et al. | |
| 2004/0209901 A1 | 10/2004 | Adams et al. | |
| 2004/0220393 A1 | 11/2004 | Ward et al. | |
| 2004/0241761 A1 | 12/2004 | Sarvetnick | |
| 2005/0037488 A1 | 2/2005 | Mitalipova | |
| 2005/0037491 A1 * | 2/2005 | Mistry et al. | 435/366 |
| 2005/0053588 A1 | 3/2005 | Yin et al. | |
| 2005/0054093 A1 * | 3/2005 | Haas | 435/366 |
| 2005/0054098 A1 | 3/2005 | Mistry et al. | |
| 2005/0054102 A1 | 3/2005 | Wobus et al. | |
| 2005/0058631 A1 | 3/2005 | Kihm et al. | |
| 2005/0063961 A1 | 3/2005 | Friedlander et al. | |
| 2005/0148070 A1 | 7/2005 | Thomson et al. | |
| 2005/0158852 A1 | 7/2005 | Wang et al. | |
| 2005/0187298 A1 | 8/2005 | Vasudevan et al. | |
| 2005/0208029 A1 | 9/2005 | Umezawa et al. | |
| 2005/0233446 A1 | 10/2005 | Parsons | |
| 2005/0244962 A1 | 11/2005 | Thomson et al. | |
| 2005/0260749 A1 | 11/2005 | Odorico et al. | |
| 2005/0266554 A1 | 12/2005 | D'Amour | |
| 2006/0003446 A1 | 1/2006 | Keller | |
| 2006/0030042 A1 | 2/2006 | Brivaniou et al. | |
| 2006/0040387 A1 | 2/2006 | Fisk | |
| 2006/0148081 A1 | 7/2006 | Kelly et al. | |
| 2006/0194315 A1 | 8/2006 | Condie et al. | |
| 2006/0194321 A1 | 8/2006 | Colman et al. | |
| 2006/0281174 A1 | 12/2006 | Xu et al. | |
| 2007/0010011 A1 | 1/2007 | Parsons | |
| 2007/0082397 A1 | 4/2007 | Hasson et al. | |
| 2007/0154981 A1 | 7/2007 | Hori et al. | |
| 2007/0155661 A1 | 7/2007 | Kim | |
| 2007/0254359 A1 | 11/2007 | Rezania | |
| 2007/0259421 A1 | 11/2007 | D'Amour et al. | |
| 2007/0259423 A1 | 11/2007 | Odorico | |
| 2007/0264713 A1 | 11/2007 | Terstegge et al. | |
| 2008/0091234 A1 | 4/2008 | Kladakis et al. | |
| 2008/0241107 A1 | 10/2008 | Copland, III et al. | |
| 2008/0268533 A1 | 10/2008 | Dalton et al. | |
| 2008/0268534 A1 | 10/2008 | Robins et al. | |
| 2009/0093055 A1 | 4/2009 | Fisk et al. | |
| 2009/0170198 A1 | 7/2009 | Rezania | |
| 2009/0203141 A1 | 8/2009 | Lin et al. | |
| 2009/0298178 A1 | 12/2009 | D'Amour | |
| 2010/0003749 A1 | 1/2010 | Uchida et al. | |
| 2010/0015100 A1 | 1/2010 | Xu | |
| 2010/0015711 A1 | 1/2010 | Davis et al. | |
| 2010/0028307 A1 | 2/2010 | O'Neil | |
| 2010/0093053 A1 | 4/2010 | Oh et al. | |
| 2010/0112693 A1 | 5/2010 | Rezania et al. | |
| 2010/0255580 A1 | 10/2010 | Rezania | |
| 2011/0014703 A1 | 1/2011 | Xu et al. | |
| 2012/0045830 A1 | 2/2012 | Green et al. | |

FOREIGN PATENT DOCUMENTS

| | | |
|---|---|---|
| EP | 0363125 A2 | 4/1990 |
| EP | 348969 B1 | 5/1993 |
| EP | 0617126 B1 | 9/1994 |
| EP | 0800829 B1 | 10/1997 |
| EP | 0092302 B1 | 11/2006 |
| EP | 1873237 A1 | 1/2008 |
| EP | 1391505 B1 | 1/2009 |
| KR | 10-2008-0020098 A | 3/2008 |
| WO | 9219759 A2 | 2/1992 |
| WO | 9847892 A1 | 10/1998 |
| WO | 9920741 A1 | 4/1999 |
| WO | 0029549 A1 | 5/2000 |
| WO | 0151616 A2 | 7/2001 |
| WO | 0181549 A3 | 11/2001 |
| WO | 0246183 A2 | 6/2002 |
| WO | 0246197 A1 | 6/2002 |
| WO | 02092756 A2 | 11/2002 |
| WO | 03026584 A2 | 4/2003 |
| WO | 03033697 A1 | 4/2003 |
| WO | 03042405 A2 | 5/2003 |
| WO | 03005049 A1 | 6/2003 |
| WO | 03054169 A1 | 7/2003 |
| WO | 03062405 A2 | 7/2003 |
| WO | 03095452 A1 | 11/2003 |
| WO | 03102134 A2 | 12/2003 |
| WO | 03103972 A1 | 12/2003 |
| WO | 2004011621 A2 | 2/2004 |
| WO | 2004016747 A2 | 2/2004 |
| WO | 2004044158 A2 | 5/2004 |
| WO | 2004050827 A2 | 6/2004 |
| WO | 2004055155 A2 | 7/2004 |
| WO | 2004073633 A1 | 9/2004 |
| WO | 2004087885 A2 | 10/2004 |
| WO | 2004090110 A2 | 10/2004 |
| WO | WO 2005/001077 A2 | 1/2005 |
| WO | 2005014799 A1 | 2/2005 |
| WO | 2005017117 A2 | 2/2005 |
| WO | 2005058301 A1 | 6/2005 |
| WO | 2005063971 A1 | 7/2005 |
| WO | 2005065354 A2 | 7/2005 |
| WO | 2005080551 A2 | 9/2005 |
| WO | 2005086845 A2 | 9/2005 |
| WO | 2005116073 A3 | 12/2005 |
| WO | 2006016999 A1 | 2/2006 |
| WO | 2006020919 A1 | 2/2006 |
| WO | 2006026473 A1 | 3/2006 |
| WO | 2006094286 A2 | 9/2006 |
| WO | 2006100490 A1 | 9/2006 |
| WO | 2006113470 A2 | 10/2006 |
| WO | 2006114098 A2 | 11/2006 |
| WO | 2006135824 A1 | 12/2006 |
| WO | 2006137787 A1 | 12/2006 |
| WO | 2006138433 A2 | 12/2006 |
| WO | 2007003525 A2 | 1/2007 |
| WO | 2007012144 A1 | 2/2007 |
| WO | 2007016485 A2 | 2/2007 |
| WO | 2007027157 A1 | 3/2007 |
| WO | 2007030870 A1 | 3/2007 |
| WO | 2007047509 A2 | 4/2007 |
| WO | 2007051038 A2 | 5/2007 |

(56) References Cited

FOREIGN PATENT DOCUMENTS

| | | |
|---|---|---|
| WO | 2007082963 A1 | 7/2007 |
| WO | 2007103282 A1 | 9/2007 |
| WO | 2007127927 A2 | 11/2007 |
| WO | 2007139929 A2 | 12/2007 |
| WO | 2007149182 A2 | 12/2007 |
| WO | 2008004990 A2 | 1/2008 |
| WO | 2008013664 A1 | 1/2008 |
| WO | 2008035110 A1 | 3/2008 |
| WO | 2008036447 A2 | 3/2008 |
| WO | 2008048647 A1 | 4/2008 |
| WO | 2008048671 A1 | 4/2008 |
| WO | 2008086005 A1 | 7/2008 |
| WO | 2008094597 | 8/2008 |
| WO | 2008102118 A1 | 8/2008 |
| WO | 2009012428 A1 | 1/2009 |
| WO | 2009018453 A1 | 2/2009 |
| WO | 2009027644 A2 | 3/2009 |
| WO | 2009070592 A1 | 6/2009 |
| WO | 2009096902 A1 | 8/2009 |
| WO | 2009101407 A2 | 8/2009 |
| WO | WO2009105570 A2 | 8/2009 |
| WO | 2009131568 A1 | 10/2009 |
| WO | 2010000415 A1 | 1/2010 |
| WO | 2011108993 A1 | 9/2011 |

OTHER PUBLICATIONS

Haruta, M. et al., "In Vitro and In Vivo Characterization of Pigment Epithelial Cells Differentiated from Primate Embryonic Stem Cells", 2004, Investig. Ophthalmol. Visual Sci. vol. 45, No. 3, pp. 1020-1025.
Kicic, A. et al., 2003, J. Neurosci. 23: 7742-7749.
Le Blanc, K., et al., "Mesenchymal Stem Cells Inhibit and Stimulate Mixed Lymphocyte Cultures and Mitogenic Response Independently of the Major Histocompatibility Complex", Scandinavian Journal of Immunology, 57 (1): 11-20 (2003).
Lund, R. D. et al., 2001, Progress in Retinal and Eye Research 20: 415-449.
Lund, R. L. et al., 2003, J. Leukocyte Biol. 74: 151-160.
Nakamura, T. & Kinoshita, S., 2003. Cornea 22 (Supp. 1): S75-S80.
Osborne et al., 2003, Eur. J. Ophthalmol, 13 (Supp 3): S19-S26.
Sakaguchi, D.S., et al., "Integration of Adult Mesenchymal Stem Cells in the CNS." Society for Neuroscience Abstract Viewer and Itinerary Planner, vol. 2002, 2002, p. Abstract No. 237.18.
Schraermeyer, U. et al., 2001, Cell Transplantation 10: 673-680.
Tomita, M. et al., 2002, Stem Cells 20: 279-283.
Tresco, P. A. et al., Technology of Mammalian Cell Encapsulation, 2000, Advanced Drug Delivery Reviews 42: pp. 29-64.
Zhang, Jie et al., "Differentiation Potential of Bone Marrow Mesenchymal Stem Cells into Retina in Normal and Laser-Injured Rat Eye", Science in China Ser. C, Life Sciences, 2004, 47(3): 241-250.
Zhang, Jie, "Differentiation of Mesenchymal Stem Cells into Retinal Structures and Effect of Mesencymal Stem Cells in Treating Severe Retinal Injuries", a doctoral thesis of Chinese PLA Academy of Military Medical Sciences, (2003).
Zubaty, V., et al.: "Transplantation of Mesenchymal Stem Cells into RCS Rats for Retinal Repair" Investigative Opthamology & Visual Science, Association for Research in Vision and Ophthamology, US, vol. 46, no. Suppl. S, (2005), p. 4160.
The Leukocyte Antigen Fact Book, 2[sup]nd edition, Barclay, A. N. et al. Academic Press, London 1997.
Vacanti, "Selective Cell Transplantation Using Bioabsorbable Artificial Polymers as Matrices", J. Pediatr. Surg. 23 (1 Pt 2): 3-9 (1988).
Vunjak-Novakovic, "Dynamic Cell Seeding of Polymers Scaffolds for Cartilage Tissue Engineering", Biotechnol. Prog. 14(2): 193-202 (1998).
Yang, "Novel Cell Immobilization Method Utilizing Centrifugal Force to Achieve High-Density Hepatocyte Culture in Porous Scaffold", J. Biomed. Mater. Res. 55(3): 379-86 (2001).
Age-Related Eye Disease Study Research Group, NEI, NIH, AREDS Report No. 8, 2001, Arch. Ophthalmol. 119:1417-1436.

Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.
Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.
Ackermann, et al., Molecular Regulation of Pancreatic B-Cell Mass Development, Maintenance, and Expansion, Journal of Molecular Endocrinology, 2007, pp. 193-206, vol. 38.
Adams, J, Proteasome Inhibition in Cancer: Development of PS-341, Seminars in Oncology, 2001, pp. 613-619, vol. 28, No. 6.
Allegrucci, et al., Differences between Human Embryonic Stem Cell Lines, Human Reproduction Update, Aug. 26, 2006, pp. 1-18, Advance Access.
Almond, et al., The Proteasome: A Novel Target for Cancer Chemotherapy, Leukemia, 2002, pp. 433-443, vol. 16.
Amit et al., Human Feeder Layers for Human Embryonic Stem Cells, Biology of Reproduction, Jan. 22, 2003, 2150-2156, 68, No. 6, Society for the Study of Reproduction, Inc.
Amit, et al., Clonally Derived Human Embryonic Stem Cell Lines Maintain Pluripotency and Proliferative Potential for Prolonged Periods of Culture, Developmental Biology, 2000, pp. 271-278, vol. 227.
Amit, et al., Feeder Layer-and Serum-Free Culture of Human Embryonic Stem Cells, Biology of Reproduction, 2004, pp. 837-845, vol. 70.
Arai, et al., Purification of Recombinant Activin A Using the Second Follistatin Domain of Follistatin-Related Gene (FLRG), Protein Expression & Purification, 2006, pp. 78-82, vol. 49.
Armstrong, et al., The Role of P13K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.
Assady, et al., Insulin Production by Human Embryonic Stem Cells, Diabetes, 2001, pp. 1691-1697, vol. 50.
Baetge, Production of B-Cells from Human Embryonic Stem Cells, Diabetes, Obesity, Metabolism, 2008, pp. 186-194, vol. 10, Supplement 4.
Balsam, et al., Haematopoeitic Stem Cells Adopt Mature Haeatopoietic Fates in Ischaemic Myocardium, Nature, Apr. 8, 2004, pp. 668-673, Nature Publishing Group.
Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.
Beltrami, et al., Adult Cardiac Stem Cells are Multipotent and Support Myocardial Regeneration, Cell, Sep. 19, 2003, pp. 763-776, vol. 114, Cell Press.
Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.
Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139, vol. 120, No. 4.
Blyszczuk et al., Expression of Pax4 in embryonic stem cells promotes differentiation of nestin-positive progenitor and insulin-producing cells, Proceedings of the National Academy of Sciences, Feb. 4, 2003, 998-1003, 100-3, National Academy of Sciences.
Bocian-Sobkowska, et al., Polyhormonal Aspect of the Endocrine Cells of the Human Fetal Pancreas, Histochem Cell Biol, 1999, pp. 147-153, vol. 112, Issue 2.
Bonner-Weir et al., In vitro cultivation of human islets from expanded ductal tissue, Proceedings of the National Academy of Sciences, Jul. 5, 2000, 7999-8004, 97-14, National Academy of Sciences.
Borowiak, et al., How to Make AB Cells, Current Opinion Cell Biology, 2009, pp. 727-732, vol. 21, Issue 6.
Borowitz, et al., Prognostic Signifigance of Fluorescence Intensity of Surface Marker . . . , Blood, Jun. 1, 1997, 3960-3966, 89-11, American Society of Hematology, Washington, D.C., US.
Braam, et al., Improved Genetic Manipulation of Human Embryonic Stem Cells, Nature Methods, May 2008, pp. 389-392, vol. 5, No. 5.

(56) References Cited

OTHER PUBLICATIONS

Brakenhoff et al., Development of a Human Interleukin-6 Receptor Antagonist, Journal of Biological Chemistry, Jan. 7, 1994, 86-93, 269-1, US.

Brambrink, et al., Sequential Expression of Pluripotency Markers During Direct Reprogramming of Mouse Somatic Cells, Cell Stem Cell, 2008, pp. 151-159, vol. 2.

Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.

Brevini, et al., No Shortcuts to Pig Embryonic Stem Cells, Theriogenology, 2010, pp. 544-550, vol. 74.

Bross, et al., Approval Summary for Bortezomib for Injection in the Treatment of Multiple Myeloma, Clinical Cancer Research, Jun. 15, 2004, pp. 3954-3964, vol. 10.

Brown, et al., Optimal Control of Blood Glucose: The Diabetic Patient or the Machine?, Science Translation Medicine, Apr. 14, 2010, pp. 1-5, vol. 2 Issue 27.

Burkard et al, Conditional Neuronal Nitric Oxide Synthase Overexpression Impairs Myocardial Contractility, Circulation Reseach, Jan. 18, 2007, pp. e32-e44, vol. 100.

Buzzard et al., Karyotype of human ES cells during extended culture, Nature Biotechnology, Apr. 1, 2004, 381-382, 22-4, Nature Publishing Group.

Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.

Castaing, et al., Blood Glucose Normalization Upon Transplantation of Human Embryonic Pancreas into Beta-Cell-Deficient SCID Mice, Diabetologica, 2001, pp. 2066-2076, vol. 44.

Chambers, et al., Functional Expression Cloning of Nanog, a Pluripotency Sustaining Factor in Embryonic Stem Cells, Cell, May 30, 2003, pp. 643-655, vol. 113.

Chen, et al., A Small Molecule that Directs Differentiation of Human ESCs into the Pancreatic Lineage, Nature Chemical Biology, Apr. 11, 2009, pp. 258-265, vol. 5, No. 4.

Chen, et al., Chemically Defined Conditions for Human iPSC Derivation and Culture, Nature Methods, 2011, pp. 424-429, vol. 8, Issue 5.

Chen, et al., Differentiation of Rat Marrow Mesencymal Stem Cells in Pancreatic Islet Beta-Cells, World Journal of Gastroenterology, Oct. 15, 2004, pp. 3016-3020.

Cheon et al., Secretory Leukocyte Protease Inhibitor (SLPI) Regulate the Embryonic Differentiation During Periimplantation Stage, Biology of Reproduction, 2007, 64, 77, Society for the Study of Reproduction, Inc.

Cheon, et al., Defined Feeder-Free Culture System of Human Embryonic Stem Cells, Biol Reprod, 2005, 105.046870, DOI10/1095.

Chung, et al., Human Embryonic Stem Cell Lines Generated without Embryo Destruction, Cell Stem Cell, 2008, pp. 113-117, vol. 2.

Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.

Crane, et al., An Embryogenic Model to Explain Cytogenetic Inconsistencies Observed in Chorionic Villus Versus Fetal Tissue, Prenatal Diagnosis, 1988, pp. 119-129, vol. 8.

Cresta, et al., Phase I Study of Bortezomib with Weekly Paclitaxel in Patients with Advanced Solid Tumours, European Journal of Cancer, 2008, pp. 1829-1834, vol. 44.

Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.

D'Amour et al., Efficient differentiation of human embryonic stem cells to definitive endoderm, Nature Biotechnology, Oct. 28, 2005, 1-8, :W.1038/nbt1163, Nature Publishing Group.

D'Amour et al., Production of pancreatic hormone-expressing endocrine cells from human embryonic stem cells, Nature Biotechnology, Oct. 19, 2006, 1392-1401, 24-11, Nature Publishing Group, US.

De Coppi, et al., Isolation of Amniotic Stem Cell Lines with Potential for Therapy, Nature Biotechnology, 2007, pp. 100-106, vol. 25, No. 1.

De Rosa, 11-color, 13-parameter flow cytometry: Identification of . . . , Nature, Feb. 1, 2001, 245-248, 7-2, Nature Publishing Group, US.

Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.

Donovan, et al., The End of the Beginning for Pluripotent Stem Cells, Nature, Nov. 2001, pp. 92-97, vol. 414.

Dorrell, et al., Editorial, Stem Cell Research, 2008, pp. 155-156, vol. 1.

Draper, et al., Recurrent Gain of Chromosomes 17q and 12 in Cultured Human Embryonic Stem Cells, Nature Biotechnology, 2004, pp. 53-54, vol. 22, No. 1.

Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.

Dupont-Gillain, et al., Plasma-Oxidized Polystyrene: Wetting Properties and Surface Reconstruction, Langmuir, 2000, pp. 8194-8200, vol. 16.

Edlund, Pancreatic Organogenisis—Pancreatic Mechanisims and Implications for Therapy, Nature, Jul. 1, 2002, 524-532, 3, Nature Publishing Group, US.

Ellerstrom, et al., Derivation of a Xeno-Free Human Embryonic Stem Cell Line, Stem Cells, 2006, pp. 2170-2176, vol. 24.

Ellerstrom, et al., Facilitated Expansion of Human Embryonic Stem Cells by Single-Cell Enzymatic Dissociation, Stem Cells, 2007, pp. 1690-1696, vol. 25, No. 7.

Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, The Endocrine Society.

Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.

Ezashi, et al., Low O2 Tensions and the Prevention of Differentiation of hES Cells, Proceedings of the National Academy of Sciences of USA, Mar. 29, 2005, pp. 4783-4788, vol. 102, No. 13.

Fauza, Amniotic Fluid and Placental Stem Cells, Ballieres Best Practice and Research Clinical Obsterics and Gynaecology, 2004, pp. 877-891, vol. 18, No. 6.

Fidler et al., Selective Immunomodulation by the Antineoplastic Agent Mitoxantrone, Journal of Immunology, Jul. 15, 1986, 727-732, 137-2, American Society of Immunologists, US.

Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.

Fok, et al., Shear-Controlled Single-Step Mouse Embryonic Stem Cell Expansion and Embryoid Body-Based Differentiation, Stem Cells, 2005, pp. 1333-1342, vol. 23.

Frandsen et al., Activin B mediated induction of Pdx1 in human embryonic stemcell derived embryoid bodies, Biochemical and Biophysical Research Communications, Aug. 15, 2007, 568-574, 362, Elsevier Inc.

Frigui, et al., A Robust Competitive Clustering Algorithm With Applications in Computer Vision, IEEE Transactions on Pattern Analysis and Machine Intelligence, May 1, 1999, pp. 450-465, vol. 21, No. 5, IEEE, US.

Fung, et al., The Effect of Medical Therapy and Islet Cell Transplantation on Diabetic Nephropathy: An Interim Report, Transplantation, Jul. 15, 2007, pp. 17-22, vol. 84, No. 1.

Gadue, et al., Wnt and TGB-B Signaling Are Required for the Induction of an in vitro Model of Primitive Streak Formation Using Embryonic Stem Cells, Proceedings of the National Academy of Sciences, Nov. 7, 2006, 16806-16811, 103-45, National Academy of Sciences, US.

(56) References Cited

OTHER PUBLICATIONS

Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.
Gellibert, et al., Identification of 1,5-Naphthyridine Derivatives as a Novel Series of Potent and Selective TGF-B Type I Receptor Inhibitor, J. Med. Chem, 2004, pp. 4494-4506, vol. 47, No. 18.
Gershengorn et al., Epithelial-to-Mesenchymal Transition Generates Proliferative Human Islet Precursor Cells, Science, Dec. 24, 2004, 2261-2264, 306, US.
Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.
Ginis, et al., Differences Between Human and Mouse Embryonic Stem Cells, Developmental Biology, 2004, pp. 360-380, vol. 269.
Gosden, et al., Amniotic Fluid Cell Types and Culture, British Medical Bulletin, 1983, pp. 348-354, vol. 39, No. 4.
Graham, et al., Characteristics of a Human Cell Line Transformed by DNA from Human Adenovirus Type 5, Journal General Virology, 1977, pp. 59-72, vol. 36.
Guo, et al., Stem Cells to Pancreatic B-Cells: New Sources for Diabetes Cell Therapy, Endocrine Reviews, May 2009, pp. 214-227, vol. 30, No. 3, The Endocrine Society.
Hadley, et al., Extracellular Matrix Regulates Sertoli Cell Differentiation, Testicular Cord Formation, and Germ Cell Development In Vitro, The Journal of Cell Biology, Oct. 1985, 1511-1522, 101, Rockefeller University Press.
Hamann, et al., Phenotypic and Functional Separation of Memory and and Effector Human CD8+ T Cells, Journal of Experimental Medicine, Mar. 11, 1997, 1407-1418, 186-9, Rockefeller University Press, US.
Harb, et al., The Rho-Rock-Myosin Signaling Axis Determines Cell-Cell Integrity of Self-Renewing Pluripotent Stem Cells, Plos One, 2008, Article e3001, XP002530386, vol. 3, Issue 8.
Hasegawa, et al., A Method for the Selection of Human Embryonic Stem Cell Sublines with High Replating Efficiency After Single-Cell Dissociation, Stem Cells, 2006, pp. 2649-2660, vol. 24.
Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.
Held, et al., The Effect of Oxygen Tension on Colony Formation and Cell Proliferation of Amniotic Fluid Cells In-Vitro, Vitro, Prenatal Diagnosis, 1984, pp. 171-180, vol. 4, No. 3.
Henderson, et al., Preimplantation Human Embryos and Embryonic Stem Cells Show Comparable Expression of Stage-Specific Embryonic Antigens, Stem Cells, 2002, pp. 329-337, vol. 20.
Heng, et al., Mechanical dissociation of human embryonic stem cell colonies by manual scraping after collagenase treatment is much more detrimental to cellular viability than is trypsinization with gentle pipetting, Biotechnol. Appl. Biochem., 2007, 33-37, 47, Portland Press Ltd., GB.
Herzenberg, et al., Fluorescence-activated Cell Sorting, Scientific American, 1976, 108-117, 234, Scientific American, US.
Hess, et al., Bone Marrow-Derived Stem Cells Initiate Pancreatic Regeneration, Nature Biotechnology, Jul. 2003, pp. 763-770, vol. 21, No. 7.
Hoehn, et al., Morphological and Biochemical Heterogeneity of Amniotic Fluid Cells in Culture, Methods in Cell Biology, 1982, pp. 11-34, vol. 26, Academic Press, Inc.
Hoffman, et al., Characterization and Culture of Human Embryonic Stem Cells, Nature Biotechnology, 2005, pp. 699-708, vol. 23, No. 6.
Hori, et al., Growth inhibitors promote differentiation of insulin-producing tissue from embryonic stem cells, Proceedings of the National Academy of Sciences, Dec. 10, 2002, 16105-16110, 99-25, National Academy of Sciences.
Hussain, et al., Stem-Cell Therapy for Diabetes Mellitus, Lancet, 2004, pp. 203-205, vol. 364.
Ianus, et al., In Vivo Derivation of Glucose-Competent Pancreatic Endocrine Cells from Bone Marrow Without Evidence of Cell Fusion, The Journal of Clinical Investigation, Mar. 2003, pp. 843-850, vol. 111, No. 6.
Inami, et al., Differentiation of Induced Pluripotent Stem Cells to Thymic Epithelial Cells by Phenotype, Immunology and Cell Biology, Jun. 24, 2010, pp. 1-8, doi:10.1038/icb.2010.96.
Inman, et al., SB-431542 is a Potent and Specific Inhibitor of Transforming Growth Factor-B Superfamily Type I Activing Receptor-Like Kinase (ALK) Receptors ALK4, ALK5, and ALK7, Molecular Pharmacology, 2002, pp. 65-74, vol. 62, No. 1.
Int' Anker, et al., Amniotic Fluid as a Novel Source of Mesenchymal Stem Cells for Therapeutic Transplantation, Blood, Aug. 15, 2003, pp. 1548-1549, vol. 102, No. 4.
Inzunza, et al., Derivation of Human Embryonic Stem Cell Lines in Serum Replacement Medium Using Postnatal Human Fibroblasts as Feeder Cells, Stem Cells, 2005, 544-549, 23, AlphaMed Press.
Jafary, et al., Differential effect of activin on mouse embryonic stem cell differentiation in insulin-secreting cells under nestin-positive selection and spontaneous differentiation protocols, Cell Biology International, 2008, 278-286, 32, Elsevier.
Jeon, et al., Endocrine Cell Clustering During Human Pancreas Development, J Histochem Cytochem, 2009, pp. 811-824, vol. 57, Issue 9.
Jiang, et al., Generation of Insulin-Producing Islet-Like Clusters from Human Embryonic Stem Cells, Stem Cells, 2007, pp. 1940-1953, vol. 25, Issue 8.
Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.
Kahan, Pancreatic Precursors and Differentiated Islet Cell Types from Murine Embryonic Stem Cells, Diabetes, Aug. 2003, pp. 2016-2042, vol. 52.
Kelly, et al., Cell-Surface Markers for the Isolation of Pancreatic Cell Types Derived from Human Embryonic Stem Cells, Nature Biotechnology, 2011, pp. 750-756, vol. 29, Issue 8.
Kingsley, The TGF-B Superfamily: New Members, New Receptors, and New Genetic Tests of Function in Different Organisms, Genes & Development, 1994, pp. 133-146, XP009011502, vol. 8, Cold Spring Harbor Laboratory Press.
Kinkel, et al., Cyp26 Enzymes Function in Endoderm to Regulate Pancreatic Field Size, PNAS, May 12, 2009, pp. 7864-7869, vol. 106, No. 19.
Kleinman et al., Basement Membrane Complexes with Biological Activity, Biochemistry, 1986, 312-318, 25, American Chemical Society.
Klimanskaya, et al., Human Embryonic Stem Cells Derived without Feeder Cells, Lancet, May 2005, pp. 1636-1641, vol. 365, No. 9471.
Koblas, et al., Differentiation of CD133-Positive Pancreatic Cells Into Insulin-Producing Islet-Like Cell Clusters, Transplantation Proceedings, 2008, pp. 415-418, vol. 40.
Kohen, et al., Characterization of Matrigel Interfaces During Defined Human Embryonic Stem Cell Culture, Biointerphases, Dec. 2009, pp. 6979.
Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.
Koyangi et al., Inhibitio nof the Rho/ROCK Pathway Reduces Apoptosis During Transplantatation of Embryonic Stem Cell-Derived Neural Precursors, Journal of Neurosciene Research, Sep. 7, 2007, 270-280, 86, Wiley-Liss, Inc.
Kozikowski, et al., New Amide-Bearing Benzolactam-Based Protein Kinase C Modulators Induce Enhanced Secretion of the Amyloid Precuros Protein Metabolite sAPPa, J. Med. Chem., 2003, pp. 364-373, vol. 46, No. 3.
Krapcho et al., Synthesis and Antineoplastic Evaluations of 5,8-Bis[(aminoalkyl)amino]-1-azaanthracene-9,10-diones, Journal of Medical Chemistry, 1985, 1124-1126, 28, American Chemical Society.

(56) References Cited

OTHER PUBLICATIONS

Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.

Kron, et al., Expression of Human Activin C Protein in Insect Larvae Infected with a Recombinant Baculovirus, Journal of Virological Methods, 1998, pp. 9-14, vol. 72.

Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.

Krutzik, et al., Coordinate Analysis of Murine Immune Cell Surface Markers and Intracellular Phosphoproteins by Flow Cytometry, Journal of Immunology, May 30, 2005, 2357-2365, 175, American Association of Immunologists, Inc., US.

Ku et al., Committing Embryonic Stem Cells to Early Endocrine Pancreas In Vitro, Stem Cells, 2004, 1205-1217, 22, AlphaMed Press.

Kubo et al., Development of definitive endoderm from embryonic stem cells in culture, Development, 2004, 1651-1662, 131, The Company of Biologists.

Lanza, et al., Characteristics and Characterization of Human Pluripotent Stem Cells, Stem Cell Anthology, 2010, pp. 141, 142, 144 and 146, 1st Edition.

Laplante, et al., RhoA/ROCK and Cdc42 Regulate Cell-Cell Contact and N-Cadherin Protein Level During Neurodetermination of P19 Embryonal Stem Cells, Journal of Neurobiology, 2004, pp. 289-307, vol. 60, No. 3.

Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.

Lavon et al., The Effect of Overexpression of Pdx1 and Foxa2 on the Differentiation of Human Embryonic Stem Cells into Pancreatic Cells, Stem Cells, 2006, 1923-1930, 24, Alpha Med Press, IL.

Lee et al., Establishment and Maintenance of Human Embryonic Stem Cell Lines on Human Feeder Cells Derived from Uterine Endometrium under Serum-Free Condition, Biology of Reproduction, Aug. 18, 2004, 42-49, 72.

Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.

Lee, et al., Protein Kinase A- and C- Induced Insulin Release from Ca2+-Insensitive Pools, Cellular Signalling, 2003, pp. 529-537, vol. 15.

Lee, et al., Retionic Acid-Induced Human Secretin Gene Expression in Neuronal Cells is Mediated by Cyclin-Dependent Kinase 1, Annals of the New York Academy of Sciences, 2006, pp. 393-398, vol. 1070.

Levenstein et al., Basic Fibroblast Growth Factor Support of Human Embryonic Stem Cell Self-Renewal, Stem Cells, Nov. 10, 2005, 568-574, 24, AlphaMed Press.

Li, et al., Generation of Rat and Human Induced Pluripotent Stem Cells by Combining Genetic Reprogramming and Chemical Inhibitors, Cell Stem Cell, Jan. 9, 2009, pp. 16-19, vol. 4.

Lilja et al., Cyclin-dependent Kinase 5 Promotes Insulin Exocytosis, Journal of Biological Chemistry, Jul. 6, 2001, 34199-34205, 36-7, JBC Papers in Press.

Lim, et al., Proteome Analysis of Conditioned Medium from Mouse Embryonic Fibroblast Feeder Layers which Support the Growth of Human Embryonic Stem Cells, Proteomics, 2002, pp. 1187-1203, vol. 2.

Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.

Loh, et al., Genomic Approaches to Deconstruct Puripotency, Annu Rev Genomics Hum Genet, 2011, pp. 165-185, vol. 12.

Ludwig, et al., Derivation of Human Embryonic Stem Cells in Defined Conditions, Nature Biotechnology, Feb. 2006, pp. 185-187, vol. 24 No. 2.

Lumelsky, et al., Differentiation of Embryonic Stem Cells to Insulin-Secreting Structures Similar to Pancreatic Islets, Science, 2001, 1389-1394, 292, HighWire Press.

Lyttle, et al., Transcription Factor Expression in the Developing Human Fetal Endocrine Pancreas, Diabetologica, 2008, pp. 1169-1180, vol. 51, Spring-Verlag.

MacFarlane, et al., Glucose Stimulates Translocation of the Homeodomain Transcription Factor PDX1 from the Cytoplasm to the Nucleus in Pancreatic B-Cells, The Journal of Biological Chemistry, 1999, pp. 1011-1016, vol. 274, No. 2.

Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.

Marshall, et al., Early Micro-and Macro-Angiopathy in the Streptozotocin, Research in Experimental Medicine, 1980, pp. 145-158, vol. 177, Springer-Verlag.

Marshall, et al., Isolation and Maintenance of Primate Embryonic Stem Cells, Methods in Molecular Biology, 2001, pp. 11-18, vol. 158.

Martin, et al., Bioreactors for Tissue Mass Culture: Design, Characterization, and Recent Advances, Biomaterials, Jul. 14, 2005, pp. 7481-7503, vol. 26.

Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.

McKiernan, et al., Directed Differentiation of Mouse Embryonic Stem Cells into Pancreatic-Like or Neuronal-and Glial-Like Phenotypes, Tissue Engineering, 2007, pp. 2419-2430, vol. 13, No. 10.

McLean et al., Activin A Efficiently Specifies Definitive Endoderm from Human Embryonic Stem Cells Only When Phosphatidylinositol 3-Kinase Signaling Is Suppressed, Stem Cells, 2007, 29-38, 25, AlphaMed Press.

McLin, et al., Repression of WNT/(szligbeta)-6atenin Signaling in the Anterior Endoderm is Essential for Liver and Pancreas Development, Development, 2007, pp. 2207-2217, vol. 134, Issue 12.

Meijer, et al., Pharmacological Inhibitors of Glycogen Synthase Kinase 3, Trends in Pharmacological Sciences, Sep. 2004, pp. 471-480, vol. 25, No. 9.

Micallef et al., Retinoic Acid Induces Pdx1-Positive Endoderm in Differentiating Mouse Embryonic Stem Cells, Diabetes, Feb. 2005, 301-305, 54, American Diabetes Association.

Miller, et al., The Pig as a Model for Human Nutrition, Annual Review of Nutrition, 1987, pp. 361-382, vol. 7, Annual Reviews Inc.

Milunsky, et al., Genetic Disorders and the Fetus: Diagnosis Prevention and Treatment, Pediatric and Developmental Pathology, 2011, pp. 84, vol. 14, Society for Pediatric Pathology.

Mitalipova, et al., Preserving the Genetic Integrity of Human Embryonic Stem Cells, Nature Biotechnology, 2005, pp. 19-20, vol. 23, No. 1.

Mitsui, et al., The Homeoprotein Nanog is Required for Maintenance of Pluripotency in Mouse Epiblast and ES Cells, Cell, May 30, 2003, pp. 631-642, vol. 113, Cell Press.

Miyamoto et al., Human Placenta Feeder Layers Support Undifferentiated Growth of Primate Embryonic Stem Cells, Stem Cells, 2004, 433-440, 22, AlphaMed Press.

Miyazaki et al., Regulated Expression of pdx-1 Promotes In Vitro Differentiation of Insulin-Producing Cells From Embryonic Stem Cells, Diabetes, Apr. 2004, 1030-1037, 53, American Diabetes Association.

Moore, et al., The Corneal Epithelial Stem Cell, DNA and Cell Biology, 2002, pp. 443-451, vol. 21, No. 5/6.

Moran, et al., Bidirectional-Barbed Sutured Knotless Running Anastomosis v Classic van Velthoven in a Model System, Journal of Endourology, 2007, pp. 1175-1177, vol. 21, No. 10.

Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.

Movassat, et al., Keratinocyte Growth Factor and Beta-Cell Differentiation in Human Fetal Pancreatic Endocrine Precursor Cells, Diabetologia, 2003, pp. 822-829, vol. 46.

(56) References Cited

OTHER PUBLICATIONS

Muchamuel, et al., Preclinical Pharmacology and in Vitro Characterization of PR-047, an Oral Inhibitor of the 20s Proteasome, Blood, Nov. 16, 2008, p. 1257, vol. 112, No. 11.
Munoz, et al., Conventional Pluripotency Markers are Unspecific for Bovine Embryonic-Derived Cell-Lines, Theriogenology, 2008, pp. 1159-1164, vol. 69.
Murtha, et al., Evaluation of a Novel Technique for Wound Closure Using a Barbed Suture, Cosmetic, Aug. 2, 2005, pp. 1769-1780, vol. 117, No. 6.
Nakagawa, et al., Generation of Induced Pluripotent Stem Cells without Myc from Mouse and Human Fibroblasts, Jan. 2008, pp. 101-106, vol. 26, No. 1.
Nicholas et al., A Method for Single-Cell Sorting and Expansion of Genetically modified Human Embryonic Stem Cells, Stem Cells and Development, 2007, 109-117, 16, Mary Ann Liebert, Inc.
Nishimura, et al., Expression of MafA in Pancreatic Progenitors is Detrimental for Pancreatic Development, Developmental Biology, 2009, pp. 108-120, vol. 333.
Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.
Odom, et al., Control of Pancreas and Liver Gene Expression by HNF Transcription Factors, Science, 2004, pp. 1378-1381, vol. 303, No. 5662.
Oh, et al., Human Embryonic Stem Cells: Technological Challenges Towards Therapy, Clinical and Experimental Pharmacology and Physiology, 2006, pp. 489-495, vol. 33.
Okita, et al., Generation of Germline-Competent Induced Pluripotent Stem Cells, Nature, Jul. 19, 2007, pp. 313-317, vol. 448.
Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.
Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.
Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.
Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.
Pancreatic Endoerm, http://www.mdsystems.com/molecule_group.aspx?g=801&r, 1 page web printout.
Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.
Pangas, et al., Production and Purification of Recombinant Human Inhibin and Activin, Journal of Endocrinology, 2002, pp. 199-210, vol. 172.
Pardo, et al., Coming CellBIND Surface: An Improved Surface for Enhanced Cell Attachment, Corning Technical Report, 2005, 8 page report, XP002530385.
Paris, et al., Equine Embryos and Embryonic Stem Cells: Defining Reliable Markers of Pluripotency, Theriogeneology, 2010, pp. 516-524, vol. 74.
Peerani, et al., Niche-Mediated Control of Human Embryonic Stem Cell Self-Renewal and Differentiation, The EMBO Journal, 2007, pp. 4744-4755, vol. 26.
Phillips, et al., Attachment and Growth of Human Embryonic Stem Cells on Microcarriers, Journal of Biotechnology, 2008, pp. 24-32, vol. 138.
Pouton, et al., Embryonic Stem Cells as a Source of Models for Drug Discovery, Nature Reviews Drug Discovery, Aug. 2007, pp. 1474-1776, vol. 6, No. 8.
Prichard, et al., Adult Adipose Derived Stem Cell Attachment to Biomaterials, Biomaterials, 2006, pp. 936-946, vol. 28, No. 6.
Prowse, et al., A Proteome Analysis of Conditioned Media from Human Neonatal Fibroblasts Used in the Maintenance of Human Embryonic Stem Cells, Proteomics, 2005, pp. 978-989, vol. 5.
Prusa, et al., Oct-4-Expressing Cells in Human Amniotic Fluid: a New Source for Stem Cell Research?, Human Reproduction, 2003, pp. 1489-1493, vol. 18, No. 7.
R&D Systems, Embryonic & Induced Pluripotent Stem Cell Transcription Factors, http://www.mdsystems.com/molecule_group.aspx?r=1&g-3041, 2 page web printout.
Rajagopal, et al., Insulin Staining of ES Cell Progeny from Insulin Uptake, Science, Jan. 17, 2003, pp. 363, vol. 299.
Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.
Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.
Rebollar, et al., Proliferation of Aligned Mammalian Cells on Laser-Nanostructured Polystyrene, Biomaterials, 2008, pp. 1796-1806, vol. 29.
Reisner, Growing Organs for Transplantation form Embryonic Precursor Tissues, Immunol. Res., 2007, pp. 261-273, vol. 38.
Reubinoff et al., Embryonic stem cell lines from human blastocysts: somatic differentiation in vitro, Nature Biotech, Apr. 18, 2000, 399-404, 18, Nature America Inc.
Rezania, Production of Functional Glucagon-Secreting-Cells from Human Embryonic Stem Cells, Diabetes, 2011, pp. 239-247, vol. 60, Issue 1.
Richards et al., Comparative Evaluation of Various Human Feeders for Prolonged Undifferentiated Growth of Human Embryonic Stem Cells, Stem Cells, 2003, 546-556, 21, AlphaMed Publlishing.
Richardson, et al., Bortezomid (PS-341): A Novel, First-in-Class Proteasome Inhibitor for the Treatement of Multiple Myeloma and Other Cancers, Cancer Control, 2003, pp. 361-369, vol. 10, No. 5.
Ricordi et al., Automated Method for Isolation of Human Pancreatic Islets, Diabetes, Apr. 1988, 413-420, 37, American Diabetes Association.
Ryan, et al., Clinical Outcomes and Insulin Secretion After Islet Transplantation with the Edmonton Protocol, Diabetes, Apr. 2001, pp. 710-719, vol. 50.
Sato et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.
Sato, et al., Manipulation of Self-Renewal in Human Embryonic Stem Cells Through a Novel Pharmacological GSK-3 Inhibitor, Methods in Molecular Biology, 2006, pp. 115-128, vol. 331.
Sato, et al., Molecular Signature of Human Embryonic Stem Cells and its Comparison with the Mouse, Developmental Biology, Apr. 23, 2003, pp. 404-413, vol. 260.
Savino et al., Generation of Interleukin-6 Receptor Antagonists by Molecular-Modeling Guided Mutagenesis of Residues Important for gp130 Activation, EMBO Journal, 1994, 1357-1367, 13-6, IT.
Schroeder, et al., Differentiation of Mouse Embryonic Stem Cells to Insulin-Producing Cells, Nature Protocols, 2005, pp. 495-507, vol. 1, No. 2.
Schuldiner, et al., Induced Neuronal Differentiation of Human Embryonic Stem Cells, Brain Research, 2001, pp. 201-205, vol. 913.
Seaberg et al., Clonal Identification of multipotent precursors from adult ~ mouse pancreas that generate neural and pancreatic lineages, Nature Biotechnology, Sep. 2004, 1115-1124, 22, Nature Publishing Group.
Segev, et al., Differentiation of Human Embryonic Stem Cells into Insulin-Producing Clusters, Stem Cells, Jan. 1, 2004, pp. 265-274.
Serafimidis, et al., Novel Effectors of Directed and Ngn3-Mediated Differentiation of Mouse Embryonic Stem Cells into Endocrine Pancreas Progenitors, Stem Cells, 2008, pp. 3-16, vol. 26.
Shackleton, et al., Generation of a Functional Mammary Gland from a Single Stem Cell, Nature, Jan. 5, 2006, pp. 84-88, XP002567665, vol. 439.

(56) References Cited

OTHER PUBLICATIONS

Shamblott et al., Derivation of pluripotent stem cells from cultured human primordial germ cells, Developmental Biology, Nov. 1998, 13726-13731, 95, National Academy of Sciences.

Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-238, vol. 343, No. 4, The Massachusetts Medical Society.

Shen, et al., The Effects of Surface Chemistry and Adsorbed Proteins on Monocyte/Macrophage Adhesion to Chemically Modified Polystyrene Surfaces, Journal of Biomedical Matter Research, 2001, pp. 336-345, vol. 57.

Sherwood, et al., Transcriptional Dynamics of Endodermal Organ Formation, Developmental Dynamics, 2009, pp. 29-42, vol. 238, Issue 1.

Shi et al., Inducing Embryonic Stem Cells to Differentiate into Pancreatic β Cells by a Novel Three-Step Approach with Activin A and All-Trans Retinoic Acid, Stem Cells, 2005, 656-662, 23, AlphaMed Press.

Shim, et al., Directed Differentiation of Human Embryonic Stem Cells Towards a Pancreatic Cell Fate, Diabetologia, 2007, pp. 1228-1238, vol. 50.

Schindler et al., A synthetic nanofibrillar matrix promotes in vivo-like organization and morphogenesis for cells in culture, Biomaterials, Apr. 18, 2005, 5624-5631, 26, Elsevier.

Shiraki et al., TGF-B Signalling Potentiates Differentiation of Embryonic Stem Cells to Pdx-1 Expressing Endodermal Cells, Genes to Cells, 2005, 503-516, 10, Blackwell Publishing Limited.

Shiraki, et al., Guided Differentiation of Embryonic Stem Cells into Pdx1-Expressing Regional-Specific Definitive Endoderm, Stem Cells, 2008, pp. 874-885, vol. 26.

Sidhu et al., Derivation of Three Clones from Human Embryonic Stem Cell Lines by FACS Sorting and Their Characterization, Stem Cells and Development, 2006, 61-69, 15, Mary Ann Liebert, Inc.

Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.

Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.

Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, 749-756, 379, Biochemical Society, GB.

Smith et al., Anti-Interleukin-6 Monocolnal Antibody Induces Regression of Human Prostate Cancer Xenografts in Nude Mice, The Prostate, Mar. 2, 2001, 47-53, 48, Wiley-Liss, Inc.

Soria et al., Insulin-Secreting Cells Derived From Embryonic Stem Cells Normalize Glycemia in Streptozotocin-Induced Diabetic Mice, Diabetes, Feb. 2000, 1-6, 49, American Diabetes Association.

Stadtfeld, et al., Defining Molecular Cornerstones During Fibroblast to iPS Cell Reprogramming in Mouse, Cell Stem Cell, Mar. 2008, pp. 230-240, vol. 2.

Stafford, et al., Retinoic Acid Signaling is Required for a Critical Early Step in Zebrafish Pancreatic Development, Current Biology, 2002, pp. 1215-1220, vol. 12, Issue 14.

Stojkovic et al., An Autogeneic Feeder Cell System That Efficiently Supports Growth of Undifferentiated Human Embryonic Stem Cells, Stem Cells, 2005, 306-314, 23, AlphaMed Press.

Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.

Sugiyama, et al., Fluorescence-Activated Cell Sorting Purification of Pancreatic Progenitor Cells, Diabetes, Obesity and Metabolism, 2008, pp. 179-185, vol. 10, Supplement 4.

Suh, et al., Characterization of His-X3-His Sites in a-Helices of Synthetic Metal-Binding Bovine Somatotropin, Protein Engineering, 1991, pp. 301-305, vol. 4, No. 3.

Sulzbacher, et al., Activin A-Induced Differentiation of Embryonic Stem Cells into Endoderm and Pancreatic Progenitors—The Influence of Differentiation Factors and Culture Conditions, Stem Cell Rev, 2009, pp. 159-173, vol. 5.

Takahashi, et al., Homogenous Seeding of Mesenchymal Stem Cells into Nonwoven Fabric for Tissue Engineering, Tissue Engineering, 2003, pp. 931-938, vol. 9, No. 5.

Takahashi, et al., Induction of Pluripotent Stem Cells from Adult Human Fibroblasts by Defined Factors, Cell, 2007, pp. 861-872, vol. 131.

Takehara, et al., Rho-Associate Kinase Inhibitor Y-27632 Promotes Survival of Cynomolgus Monkey Embryonic Stem Cells, Molecular Human Reproduction, 2008, pp. 627-634, vol. 14, No. 11.

Tang, et al., Reprogramming Liver-Stem WB Cells into Functional Insulin-Producing Cells by Persistent Expression of Pdx1-and Pdx1-VP16 Mediated by Lentiviral Vectors, Laboratory Investigation, 2006, pp. 83-93, vol. 86.

Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, 1756-1764, 14-6, American Society of Clinical Oncology, US.

Teare, et al., Cellular Attachment to Ultraviolet Ozone Modified Polystyrene Surfaces, Langmuir, 2000, pp. 2818-2824, vol. 16.

Thomson et al., Embryonic Stem Cell Lines Derived from Human Blastocysts, Science, Nov. 6, 1998, 1145-1147, 282, HighWire Press.

Thomson et al., Isolation of a primate embryonic stem cell line, Developmental Biology, Aug. 1995, 7844-7848, 92, Proc. Natl. Acad. Sci, US.

Thomson et al., Primate Embryonic Stem Cells, Current Topics in Developmental Biology, 1998, 133-154, 38, Academic Press, US.

Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.

Tulachan et al., TGF-β isoform signaling regulates secondary transition and mesenchymal-induced endocrine development in the embryonic mouse pancreas, Developmental Biology, 2007, 508-521, 305, Elsevier.

Ubeda et al., Inhibition of Cyclin-dependent Kinase 5 Activity Protects Pancreatic Beta Cells from Glucotoxicity, Journal of Biological Chemistry, Aug. 3, 2006, 28858-28864, 39, JBC Papers in Press.

Ungrin, et al., Reproducible, Ultra High-Throughput Formation of Multicellular Organization from Single Cell Suspension-Derived Human Embryonic Stem Cell Aggregates, Plos ONE, 2008, e1565, pp. 1-12, vol. 3, Issue 2.

Unknown, MeSH Descriptor Data, National Library of Medicine—Medical Subject Headings, Feb. 26, 1992, XP002553615.

Unknown, Preserve the Stability of Your Stem Cells, Stem Cells, 2006, Internet Citation, XP002496166.

Valet, et al., Pretherapeutic Identification of High-Risk Acute Myeloid Leukemia (AML) Patients from . . . , Clinical Cytometry, Feb. 17, 2003, 4-10, 53B, Wiley-Liss, Inc., US.

Vallier, et al., Activin/Nodal and FGF Pathways Cooperate to Maintain Pluripotency of Human Embryonic Stem Cells, Journal of Cell Sciences, 2005, pp. 4495-4509, vol. 118.

Van Der Greef et al., Rescuing drug discovery: in vivo systems pathology and systems pharmacology, Nature, Dec. 1, 2005, 961-967, 4-1, Nature Reviews, US.

Van Der Windt, et al., The Chioce of Anatomical Site for Islet Transplantation, Cell Transplantation, 2008, pp. 1005-1014, vol. 17.

Van Kooten, et al., Plasma-Treated Polystyrene Surfaces: Model Surfaces for Studying Cell-Biomaterial Interactions, Biomaterials, 2004, pp. 1735-1747, vol. 25.

Van Wachem, et al., Vacuum Cell Seeding: a NewMethod for the Fast Application of an Evenly Distributed Cell Layer on Porous Vascular Grafts, Biomaterials, 1990, pp. 602-606, vol. 11.

Vanderford et al., Multiple kinases regulate mafA expression in the pancreatic beta cell line MIN6, Biochemistry and Biophysics, 2008, 138-142, 480, Elsevier.

Verfaillie, et al., Stem Cells: Hype and Reality, Hematology, 2002, pp. 369-391.

(56) References Cited

OTHER PUBLICATIONS

Vodicka, et al., The Miniature Pig as an Animal Model in Biomedical Research, Annals New York Academy of Sciences, 2005, pp. 161-171, vol. 1049.
Wang et al., Derivation and Growing Human Embryonic Stem Cells on Feeders Derived from Themselves, Stem Cells, 2005, 1221-1227, 23, AlphaMed Press.
Wang et al., Relationship of Chemical Structures of Anthraquinones with their Effects on the Suppression of Immune Responses, International Journal of Immunopharmacology, 1987, 733-739, 9-6, International Society for Immunopharmacology, GB.
Wang, et al., Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.
Watanabe, et al., A Rock Inhibitor Permits Survival of Dissociated Human Embryonic Stem Cells, Nature Biotechnology, 2007, pp. 681-686, vol. 25, No. 6.
Wei et al., Cdk5-dependent regulation of glucose-stimulated insulin secretion, Nature Medicine, Sep. 11, 2005, 1104-1108, 11-10, Nature Publishing Group.
Wei, et al., Human Amnion-Isolated Cells Normalize Blood Glucose in Strepozotocin Induced Diabetic Mice, Cell Transplantation, 2003, pp. 545-552, vol. 12, No. 5.
Wei, et al., Transcriptome Profiling of Human and Murine ESCs Identifies Divergent Paths Required to Maintain the Stem Cell State, Stem Cells, 2005, pp. 166-185, vol. 23.
Wells, et al., Early Mouse Endoderm is Patterned by Soluble Factors from Adjacent Germ Layers, Development, 2000, pp. 1563-1572, vol. 127, Issue 8.
Wernig, et al., c-Myc is Dispensable for Direct Reprogramming of Mouse Fibroblasts, Cell Stem Cell, Jan. 2008, pp. 10-12, vol. 2.
Wiles et al., Embryonic Stem Cell Development in a Chemically Defined Medium, Experimental Cell Research, 1999, 241-248, 247, Academic Press.
Wilson, et al., The HMG Box Transcription Factor Sox4 Contributes to the Development of the Endcrine Pancreas, Diabetes, 2005, pp. 3402-4309, vol. 54, Issue 12.
XP002553616_1989, RecName: Full=Inhibin beta B Chain; AltName: Full=Activin beta-B chain; Flags; Precurso, Database UniProt [Online], Jul. 1, 1989, Database Accession No. P09529, EBI Accession No. Uniprot: P09529.
Xu et al., Immortalized Fibroblast-Like Cells Derived from Human Embryonic Stem Cells Support Undifferentiated Cell Growth, Stem Cells, 2004, 972-980, 22, AlphaMed Press.
Xu, et al., Basic FGF and Suppression of BMP Signalling Sustain Undifferentiated Proliferation of Human ES Cells, Nature Methods, 2005, pp. 185-189, vol. 2, Issue 3.
Xu, et al., Feeder-free Growth of Undifferentiated Human Embryonic Stem Cells, Nature Biotechnology, 2001, pp. 971-974, vol. 19.
Yang, et al., Survival of Pancreatic Islet Xenografts in NOD Mice with the Theracyte Device, Transplantation Proceedings, 2002, pp. 3349-3350, vol. 34.
Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.
Yoneda, et al., The Rho Kinases I and II Regulate Different Aspects of Myosin II Activity, The Journal of Cell Biology, 2005, pp. 443-445, vol. 170, No. 3.
Young, et al., Three-Dimensional Culture of Human Uterine Smooth Muscle Nyocytes on a Resorbably Scaffolding, Tissue Engineering, 2003, pp. 451-459, vol. 9, No. 3.
Yu, et al., Induced Pluripotent Stem Cell Lines Derived from Human Somatic Cells, Science, Dec. 21, 2007, pp. 1917-1920, vol. 318.
Yu, et al., Isolation of a Novel Population of Multipotent Adult Stem Cells from Human Hair Follicles, American Journal of Pathology, Jun. 6, 2006, pp. 1879-1888, vol. 168, No. 6.
Zembower, et al., Peptide Boronic Acids Versatile Synthetic Ligands for Affinity Chromatography of Serine Proteinases, International Journal Peptide Protein, 1996, pp. 405-413, vol. 47.
Zhang et al., MafA Is a Key Regulator of Glucose-Stimulated Insulin Secretion, Molecular and Cellular Biology, Jun. 2005, 4969-4976, 25-12, American Society for Microbiology.
Zhang et al, Highly Efficient Differentiation of Human ES Cells and iPS Cells into Mature Pancreatic Insulin-Producing Cells, Cell Research, 2009, pp. 429-438, vol. 19, Issue 14.
Zhao et al., The Islet B Cell-enriched MafA Activator is a Key Regulator of Insulin Gene Transcription, Journal of Biological Chemistry, Mar. 25, 2005, 11887-11894, 280-12, The American Society for Biochemistry and molecular Biology, Inc.
Zhao, et al., Derivation and Characterization of Hepatic Progenitor Cells from Human Embryonic Stem Cells, PLoS ONE Hepatic Progenitors from hESCs, Jul. 2009, e6468 pp. 1-10, vol. 4, Issue 7.
Zorn, et al., Vertebrate Endoderm Development and Organ Formation, Annual Review Cell Development Biology, 2009, pp. 221-251, vol. 25.
Cai, J. et al., "Stem cell and precursor cell therapy," NeuroMolecular Medicine, 2002; 3:233-249.
Morigi, M. et al., "Mesenchymal Stem Cells are Renotropic, Helping to Repair the Kidney and Improve Function in Acute Renal Failure," J. Am. Soc. Nephrol., 2004; 15:1794-1804.
Schouten, J.W. et al., "A Review and Rationale for the Use of Cellular Transplantation as a Therapeutic Strategy for Traumatic Brain Injury," Journal of Neurotrauma, 2004; 21(11):1501-1538.

\* cited by examiner

CELLULAR THERAPY FOR OCULAR DEGENERATION

This present application claims the benefit of priority to U.S. Provisional Application Ser. No. 60/688,637 filed Jun. 8, 2005.

FIELD OF THE INVENTION

This invention relates to the field of cell-based or regenerative therapy for ophthalmic diseases and disorders. In particular, the invention provides mesenchymal stem cells, and methods, optionally with pharmaceutical compositions, devices for the regeneration or repair of cells and tissues of the eye.

BACKGROUND

As a complex and sensitive organ of the body, the eye can experience numerous diseases and other deleterious conditions that affect its ability to function normally. Many of these conditions are associated with damage or degeneration of specific ocular cells, and tissues made up of those cells. As one example, diseases and degenerative conditions of the optic nerve and retina are the leading causes of blindness throughout the world. Damage or degeneration of the cornea, lens and associated ocular tissues represent another significant cause of vision loss. The retina contains seven layers of alternating cells and processes that convert a light signal into a neural signal. The retinal photoreceptors and adjacent retinal pigment epithelium (RPE) form a functional unit that, in many disorders, becomes unbalanced due to genetic mutations or environmental conditions (including age). This results in loss of photoreceptors: through apoptosis or secondary degeneration, which leads to progressive deterioration of vision and, in some instances, to blindness (for a review, see, e.g., Lund, R. D. et al., 2001, Progress in Retinal and Eye Research 20: 415-449). Two classes of ocular disorders that fall into this pattern are age-related macular degeneration (AMD) and retinitis pigmentosa (RP).

AMD is the most common cause of vision loss in the United States in those 50 or older; and its prevalence increases with age. The primary disorder in AMD appears to be due to RPE dysfunction and changes in Bruch's membranes, e.g., lipid deposition, protein cross-linking and decreased permeability to nutrients (Lund et al., 2001). A variety of elements may contribute to macular degeneration, including genetic makeup, age, nutrition, smoking and exposure to sunlight.

RP is mainly considered an inherited disease: over 100 mutations have been associated with photoreceptor loss (Lund et al., 2001). Though the majority of mutations target photoreceptors, some affect RPE cells directly. Together, these mutations affect such processes as molecular trafficking between photoreceptors and RPE cells and phototransduction, for example.

Other less common, but nonetheless debilitating retinopathies can also involve progressive cellular degeneration leading to vision loss and blindness. These include, for example, diabetic retinopathy and choroidal neovascular membrane (CNVM). Diabetic retinopathy may be classified as (1) non-proliferative or background retinopathy, characterized by increased capillary permeability, edema, hemorrhage, microaneurysms, and exudates, or 2) proliferative retinopathy, characterized by neovascularization extending from the retina to the vitreous, scarring, fibrous tissue formation, and potential for retinal detachment. In CNVM, abnormal blood vessels stemming from the choroid grow up through the retinal layers. The fragile new vessels break easily, causing blood and fluid to pool within the layers of the retina.

Damage or progressive degeneration of the optic nerve and related nerves of the eye constitutes another leading cause of vision loss and blindness. A prime example is glaucoma, a condition of the eye that is made up of a collection of eye diseases that cause vision loss by damage to the optic nerve. Elevated intraocular pressure (IOP) due to inadequate ocular drainage is a primary cause of glaucoma, but it can also develop in the absence of elevated IOP.

Glaucoma can develop as the eye ages, or it can occur as the result of an eye injury, inflammation, tumor, or in advanced cases of cataract or diabetes, or it can be caused by certain drugs, such as, for example steroids. The primary features of the optic neuropathy in glaucoma include characteristic changes in the optic nerve head, a decrease in number of surviving retinal ganglion cells, and loss of vision. It has been proposed that a cascade of events links degeneration of the optic nerve head with the slow death of retinal ganglion cells observed in the disease, and that this cascade of events can be slowed or prevented through the use of neuroprotective agents (Osborne et al., 2003, Eur. J. Ophthalmol, 13 (Supp 3): S19-S26).

Cellular damage and degenerative conditions also affect other parts of the eye. For example, cataracts result from gradual opacification of the crystalline lens of the eye. It is believed that once begun, cataract development proceeds along one or more common pathways that culminate in damage to lens fibers. This condition is presently treated by surgical removal and replacement of the affected lens. Another example concerns the cornea and surrounding conjuctiva that make up the ocular surface. The limbal epithelium, located between the cornea and the bulbar conjuctiva, contains corneal epithelial stem cells. Limbal epithelial cell deficiency (LECD) is a condition that occurs, for example, in Stevens-Johnson syndrome and thermal or chemical burns. LECD often leads to an imbalance between the corneal epithelium and the conjunctival epithelium in which the cornea is covered by invading conjunctival epithelial cells, which severely compromises the corneal surface and affects visual acuity (Nakamura, T. & Kinoshita, S., 2003. Cornea 22 (Supp. 1): S75-S80).

The recent advent of stem cell-based therapy for tissue repair and regeneration provides promising treatments for a number of aforementioned cell-degenerative pathologies and other ocular disorders. Stem cells are capable of self-renewal and differentiation to generate a variety of mature cell lineages. Transplantation of such cells can be utilized as a clinical tool for reconstituting a target tissue, thereby restoring physiologic and anatomic functionality. The application of stem cell technology is wide-ranging, including tissue engineering, gene therapy delivery, and cell therapeutics, i.e., delivery of bio-therapeutic agents to a target location via exogenously supplied living cells or cellular components that produce or contain those agents (For a review, see Tresco, P. A. et al., 2000, Advanced Drug Delivery Reviews 42: 2-37).

An obstacle to realization of the therapeutic potential of stem cell technology has been difficulty in obtaining sufficient numbers of stem cells. One source of stem cells is embryonic or fetal tissue. Embryonic stem and progenitor cells have been isolated from a number of mammalian species, including humans, and several such cell types have been shown capable of self-renewal and expansion, as well differentiation into a variety of cell lineages. In animal model systems, embryonic stem cells have been reported to differentiate into a RPE cell phenotype, as well as to enhance the survival of host photoreceptors following transplantation (Haruta, M. et al., 2004, Investig. Ophthalmol. Visual Sci. 45: 1020-1025; Schraermeyer, U. et al., 2001, Cell Transplantation 10: 673-680). But the derivation of stem cells from embryonic or fetal sources has raised many ethical issues that are desirable to avoid by identifying other sources of multipotent or pluripotent cells.

Adult tissue also can yield stem cells useful for cell-based ocular therapy. For instance, retinal and corneal stem cells themselves may be utilized for cell replacement therapy in the eye. In addition, neural stem cells from the hippocampus have been reported to integrate with the host retina, adopting certain neural and glial characteristics (see review of Lund, R. L. et al., 2003, J. Leukocyte Biol. 74: 151-160). Neural stem cells prepared from fetal rat cortex were shown to differentiate along an RPE cell pathway following transplantation into the adult rat subretinal space (Enzmann, V. et al., 2003, Investig. Ophthalmol. Visual Sci.: 5417-5422).

Bone marrow stem cells have been reported to differentiate into retinal neural cells and photoreceptors following transplantation into host retinas (Tomita, M. et al., 2002, Stem Cells 20: 279-283; Kicic, A. et al., 2003, J. Neurosci. 23: 7742-7749). Kicic, A. et al. reports that $CD90^+$ mesenchymal stem cells were capable of integrating into the host retina. These cells underwent differentiation, forming structures similar to the photoreceptor layer and expressed a photoreceptor-specific marker.

Friedlander et al (published U.S. Patent Application US2005/0063961, assigned to The Scripps Research Institute, Calif.) report the rescue of blood vessels and neuronal networks in the eye by the injection of $Lin^-/CD31^+$ hematopoetic stem cells into the eye.

An ocular surface reconstruction in a rabbit model system, utilizing cultured mucosal epithelial stem cells, has also been reported (Nakamura, T. & Kinoshita, S., 2003, supra). While these reports show promise for the use of adult progenitor and stem cells in cell-based therapy for the eye, it must be noted that adult stem cell populations are comparatively rare and are often obtainable only by invasive procedures.

Further, adult stem cells may have a more limited ability to expand in culture than do embryonic stem cells. Thus, a need exists for alternative sources of adequate supplies of cells having the ability to support, augment or replace lost cellular function in the eye. A reliable, well-characterized and plentiful supply of substantially homogeneous populations of such cells would be an advantage in a variety of diagnostic and therapeutic applications in ocular repair and regeneration, including drug screening assays, ex vivo or in vitro trophic support of ocular and other useful cell types, and in vivo cell-based therapy.

To this end, the present invention is directed toward the use of cell lines as a therapy for ocular disease. Several cell lines were tested in a rodent model of retinitis pigmentosa, according to methods disclosed in published U.S. Patent Application US2005/0037491. The present invention describes the use of human mesenchymal stem cells as being useful as a therapy for ocular disease.

SUMMARY

This invention provides compositions and methods applicable to cell-based or regenerative therapy for ophthalmic diseases and disorders. In particular, the invention features mesenchymal stem cells, optionally with pharmaceutical compositions or devices for the repair or regeneration of cells or tissues of the eye. Once transplanted to a target location in the eye, the mesenchymal stem cells of the invention may provide trophic support for ocular cells in situ, or they may themselves differentiate into one or more phenotypes, or they may exert a beneficial effect in both of those fashions, but the cells do not form structures similar to the photoreceptor layer and do not express a photoreceptor-specific marker, such as rhodopsin.

One aspect of the invention features a method of treating a patient having an ocular degenerative condition, which comprises administering to the patient multipotent or pluripotent mesenchymal stem cells, in an amount effective to treat the ocular degenerative condition. In certain embodiments, the ocular degenerative condition is an acute ocular degenerative condition such as brain trauma, optic nerve trauma or ocular lesion. In other embodiments, it is a chronic or progressive degenerative condition, such as macular degeneration, retinitis pigmentosa, diabetic retinopathy, glaucoma, a limbal epithelial cell deficiency, or a retinal pigment epithelial cell deficiency. In certain embodiments, the cells are induced in vitro to differentiate into a neural or epithelial lineage cells prior to administration.

In one embodiment, the mesenchymal stem cells promote the survival or proliferation of endogenous photoreceptors in the eye. In an alternate embodiment, the mesenchymal stem cells promote the differentiation of endogenous stem cells or precursor cells to photoreceptors.

In one embodiment, the mesenchymal stem cells are positive for the expression of at least one of the following markers: CD29, CD44, CD105 or CD166. The cells are negative for the expression of at least one of the following markers: CD14, CD34 or CD45.

In certain embodiments, the cells may be administered with at least one other cell type, such as, for example, an astrocyte, an oligodendrocyte, a neuron, a neural progenitor cell, a neural stem cell, a retinal epithelial stem cell, a corneal epithelial stem cell, or an other multipotent or pluripotent stem cell. In these embodiments, the other cell type may be administered simultaneously with, or before, or after, the mesenchymal stem cells. Likewise, in these and other embodiments, the cells may be administered with at least one other agent, such as a drug for ocular therapy, or another beneficial pharmaceutical agent such as, for example, an anti-inflammatory agent, an anti-apoptotic agent, an antioxidant or a growth factor. In these embodiments, the other agent may be administered simultaneously with, before, or after, the mesenchymal stem cells.

The mesenchymal stem cell suitable for use in the present invention may be derived from tissues such as, for example, bone marrow, umbilical cord blood, amniotic sac and fluid, placenta, skin, fat, muscle, vasculature, liver, pancreas, or peripheral blood. The cells may be xenogeneic, allogeneic or autologous in origin. The cells may be isolated from the donor and transplanted immediately. Alternatively, the cells may be expanded in vitro prior to transplantation.

The cells of the present invention may be cryogenically stored. Prior to transplantation, the cells may be thawed and transplanted immediately. Alternatively, the thawed cells may be cultured and/or expanded in vitro prior to transplantation. Alternatively, the cells may be transplanted as a frozen pellet.

In various embodiments, the cells may be administered to the surface of an eye, or they may be administered to the interior of an eye or to a location in proximity to the eye, such as, for example, behind the eye, or the sub-retinal space.

The cells may be administered through a cannula or from a device implanted in the patient's body within or in proximity to the eye, or they may be administered by implantation of a matrix or support containing the cells.

Another aspect of the invention features a pharmaceutical composition for treating a patient having an ocular degenerative condition, comprising a pharmaceutically acceptable carrier and the mesenchymal stem cells of the present invention in an amount effective to treat the ocular degenerative condition. The ocular degenerative condition may be an acute, chronic or progressive condition. In certain embodiments, the composition comprises the mesenchymal cells of the present invention that have been induced in vitro to differentiate into a neural or epithelial lineage cells prior to formulation of the composition. Alternatively, the composition comprises the mesenchymal stem cells of the present invention that differentiate into a neural or epithelial lineage cells in situ, post transplantation.

In certain embodiments, the pharmaceutical composition may comprise at least one other cell type, such as an astrocyte, an oligodendrocyte, a neuron, a neural progenitor cell, a neural stem cell, a retinal epithelial stem cell, a corneal epithelial stem cell, or an other multipotent or pluripotent stem cell. In these or other embodiments, the pharmaceutical composition may comprise at least one other agent, such as a drug for treating the ocular degenerative disorder or other beneficial pharmaceutical agents, such as, for example, anti-inflammatory agents, anti-apoptotic agents, antioxidants or growth factors.

In certain embodiments, the pharmaceutical compositions may be formulated for administration to the surface of an eye. Alternatively, they may be formulated for administration to the interior of an eye or in proximity to the eye (e.g., behind the eye). The compositions may also be formulated as a matrix or support containing the cells.

According to yet another aspect of the invention, a kit is provided for treating a patient having an ocular degenerative condition. The kit may comprise a pharmaceutically acceptable carrier, a population of mesenchymal stem cells, and instructions for using the kit in a method of treating the patient. The kit may also contain one or more additional components, such as reagents and instructions for culturing the cells, or a population of at least one other cell type, or one or more agents useful in the treatment of an ocular degenerative condition.

Another aspect of the invention features a method for increasing the survival, growth or activity of cells for transplantation to treat an ocular degenerative disorder. The method comprises contacting mesenchymal stem cells with at least one pharmaceutical agent, such as, for example, growth factors, trophic factors, conditioned medium, anti-inflammatory agents, anti apoptotic agents, antioxidants, neurotrophic factors or neuroregenerative or neuroprotective drugs. Alternatively, the method may comprise co-culturing mesenchymal stem cells with at least one other cell type, such as an astrocyte, an oligodendrocyte, a neuron, a neural progenitor cell, a neural stem cell, a retinal epithelial stem cell, a corneal epithelial stem cell, or other multipotent or pluripotent stem cell, prior to transplantation. Agents, such as, for example, growth factors, trophic factors, conditioned medium, anti-inflammatory agents, anti apoptotic agents, antioxidants, neurotrophic factors or neuroregenerative or neuroprotective drugs may be added. A kit for practicing the method is also provided. The kit comprises mesenchymal stem cells and instructions for treating the cells with the at least one agent effective to increase the survival, growth or activity of the cells for transplantation. The kit may include at least one other cell type and instructions on the co-culture of the at least one other cell type with mesenchymal stem cells.

DETAILED DESCRIPTION

Figure 1:
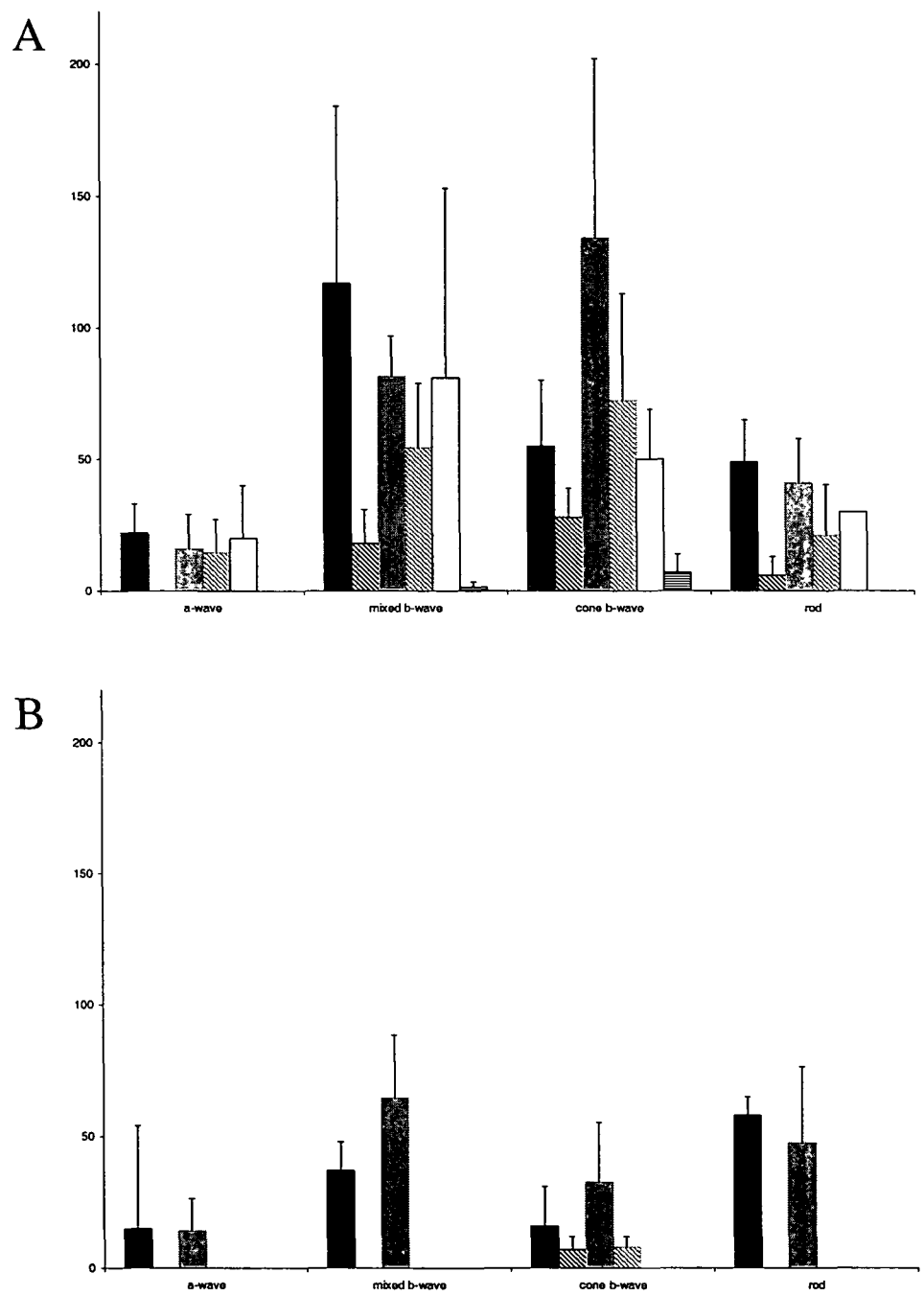
FIG. 1: Summary of ERG recordings from RCS rats receiving cellular transplants. Data shown is the mean amplitude of the ERG recordings (mV) obtained from rats at 60 (panel A) and 90 days (panel B) post transplantation (n=5 animals per condition). Recordings were taken from the eyes of rats receiving umbilical-derived cells (black bars) and the contralateral sham operated eye (black hashed bars). Recordings were taken from the eyes of rats receiving Cambrex MSC's (POIETICS™, Cat. No PT-2501) (gray bars) and the contralateral sham operated eye (gray hashed bars). Recordings were taken from the eyes of rats receiving placental-derived cells (white bars) and the contralateral sham operated eye (gray horizontally striped bars).

The terms "ocular", "ophthalmic" and "optic" are used interchangeably herein to define "of, or about, or related to the eye." The term "ocular degenerative condition" (or "disorder") is an inclusive term encompassing acute and chronic conditions, disorders or diseases of the eye, inclusive of the neural connection between the eye and the brain, involving cell damage, degeneration or loss. An ocular degenerative condition may be age-related, or it may result from injury or trauma, or it may be related to a specific disease or disorder. Acute ocular degenerative conditions include, but are not limited to, conditions associated with cell death or compromise affecting the eye including conditions arising from cerebrovascular insufficiency, focal or diffuse brain trauma, diffuse brain damage, infection or inflammatory conditions of the eye, retinal tearing or detachment, intra-ocular lesions (contusion penetration, compression, laceration) or other physical injury (e.g., physical or chemical burns). Chronic ocular degenerative conditions (including progressive conditions) include, but are not limited to, retinopathies and other retinal/macular disorders such as retinitis pigmentosa (RP), age-related macular degeneration (AMD), choroidal neovascular membrane (CNVM); retinopathies such as diabetic retinopathy, occlusive retinopathy, sickle cell retinopathy and hypertensive retinopathy, central retinal vein occlusion, stenosis of the carotid artery, optic neuropathies such as glaucoma and related syndromes; disorders of the lens and outer eye, e.g., limbal stem cell deficiency (LSCD), also referred to as limbal epithelial cell deficiency (LECD), such as occurs in chemical or thermal injury, Steven-Johnson syndrome, contact lens-induced keratopathy, ocular cicatricial pemphigoid, congenital diseases of aniridia I or ectodermal dysplasia, and multiple endocrine deficiency-associated keratitis. The term treating (or treatment of) an ocular degenerative condition refers to ameliorating the effects of, or delaying, halting or reversing the progress of, or delaying or preventing the onset of, an ocular degenerative condition as defined herein.

The term "effective amount" refers to a concentration or amount of a reagent or pharmaceutical composition, such as a growth factor, differentiation agent, trophic factor, cell population or other agent, that is effective for producing an intended result, including cell growth and/or differentiation in vitro or in vivo, or treatment of ocular degenerative conditions, as described herein. With respect to growth factors, an effective amount may range from about 1 nanogram/milliliter to about 1 microgram/milliliter. With respect to MSC's as administered to a patient in vivo, an effective amount may range from as few as several hundred or fewer to as many as several million or more. In specific embodiments, an effective amount may range from 103, more specifically at least about 104 cells. It will be appreciated that the number of cells to be administered will vary depending on the specifics of the disorder to be treated, including but not limited to size or total volume/surface area to be treated, as well as proximity of the site of administration to the location of the region to be treated, among other factors familiar to the medicinal biologist.

The terms "effective period" (or "time") and "effective conditions" refer to a period of time or other controllable conditions (e.g., temperature, humidity for in vitro methods), necessary or preferred for an agent or pharmaceutical composition to achieve its intended result.

The term "patient" or "subject" refers to animals, including mammals, preferably humans, who are treated with the pharmaceutical compositions or in accordance with the methods described herein.

A "stem cell" as used herein refers undifferentiated cells defined by the ability of a single cell both to self-renew, and to differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation, and to contribute substantially to most, if not all, tissues following injection into blastocysts.

Stem cells may be totipotent, pluripotent, multipotent, oligopotent, or unipotent. Totipotent cells are able to give rise to all embryonic and extraembryonic cell types. Pluripotent cells are able to give rise to all embryonic cell types. Multipotent cells include those able to give rise to a subset of cell lineages, but all within a particular tissue, organ, or physiological system (for example, hematopoietic stem cells (HSC) can produce progeny that include HSC (self-renewal), blood cell-restricted oligopotent progenitors, and all cell types and elements (e.g., platelets) that are normal components of the blood). Cells that are oligopotent can give rise to a more restricted subset of cell lineages than multipotent stem cells; and cells that are unipotent are able to give rise to a single cell lineage (e.g., spermatogenic stem cells). Stem cells are also categorized on the basis of the source from which they may be obtained. An adult stem cell is generally a multipotent undifferentiated cell found in tissue comprising multiple differentiated cell types. The adult stem cell can renew itself. Under normal circumstances, it can also differentiate to yield the specialized cell types of the tissue from which it originated, and possibly other tissue types.

"Mesenchymal stem cell" ("MSC") refers to a cell originating from the mesoderm of a mammal that is not fully differentiated and has the potential to differentiate into a variety of cells or tissues, including: connective tissue, bone, and cartilage, muscle, blood and blood vessels, lymphatic and lymphoid organs, notochord, pleura, pericardium, kidney, and gonads.

A "progenitor cell" refers to a cell that is derived from a stem cell by differentiation and is capable of further differen-tiation to more mature cell types. Progenitor cells typically have more restricted proliferation capacity as compared to stem cells.

By "conditioned media" is meant that a population of cells in grown in a medium and contribute soluble factors to the medium. In one such use, the cells are removed from the medium however the soluble factors produced by these cells remain. This medium is then used to nourish a different population of cells in the presence of the soluble factors produced by the initial population of cells.

"Markers" as used herein, are nucleic acid or polypeptide molecules that are differentially expressed in a cell of interest. In this context, differential expression means an increased level of the marker for a positive marker, and a decreased level for a negative marker. The detectable level of the marker nucleic acid or polypeptide is sufficiently higher or lower in the cells of interest, compared to other cells, such that the cell of interest can be identified and distinguished from other cells, using any of a variety of methods known in the art.

"Cluster of Differentiation" (CD) molecules are markers on the cell surface, as recognized by specific sets of antibodies, used to identify the cell type, stage of differentiation and activity state of a cell. Function and designation of CD markers are well established in the art. See, e.g., The Leukocyte Antigen Fact Book, $2^{nd}$ edition, Barclay, A. N. et al. Academic Press, London 1997.

"CD14" is is a high affinity receptor for the complex of lipopolysaccharids (LPS) and LPS-Binding protein (LBP). The CD14 antigen is part of the functional heteromeric LPS receptor complex comprised of CD14, TLR4 and MD-2. CD14 is strongly expressed on most human monocytes and macrophages in peripheral blood, other body fluids and various tissues, such as lymph nodes and spleen. CD14 is weakly expressed on subpopulations of human neutrophils and myeloid dendritic cells.

"CD29" is also referred to as "ibronectin receptor, beta polypeptide".

"CD34" is a transmembrane glycoprotein constitutively expressed on endothelial cells and on hematopoietic stem cells. This highly O-glycosylated molecule, containing serine and threonine-rich mucin like domains, binds to L-selectin.

"CD44" is also referred to as "Hermes antigen" and is the main cell surface receptor for hyaluronan. This CD is primarily expressed in most cell types, except for tissues/cells such as hepatocytes, some epithelial cells, and cardiac muscle.

"CD45" refers to the leukocyte common antigen having a sequence disclosed in Genbank Accession No. Y00638, or a naturally occurring variant sequence thereof (e.g., allelic variant).

"CD105" is also referred to as "Endoglin" and is primarily expressed on endothelial cells, monocytes, macrophages, stromal cells, and bone marrow mesenchymal cells.

"CD166" is a type 1 glycoprotein expressed on activated T cells, B cells and monocytes and appears to be the ligand for CD6 (1,2). Human CD166 may be important for activation of T cells.

The term "pharmaceutically acceptable carrier" (or "medium"), which may be used interchangeably with the term "biologically compatible carrier" or "medium", refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio.

Several terms are used herein with respect to cell replacement therapy. The terms "autologous transfer", "autologous transplantation", "autograft" and the like, refer to treatments wherein the cell donor is also the recipient of the cell replacement therapy. The terms "allogeneic transfer", "allogeneic transplantation", "allograft" and the like, refer to treatments wherein the cell donor is of the same species as the recipient of the cell replacement therapy, but is not the same individual. A cell transfer in which the donor's cells and have been histocompatibly matched with a recipient is sometimes referred to as a "syngeneic transfer". The terms "xenogeneic transfer", "xenogeneic transplantation", "xenograft" and the like, refer to treatments wherein the cell donor is of a different species than the recipient of the cell replacement therapy.

Isolation and Characterization of Mesenchymal Stem Cells.

Mesenchymal stem cells suitable for use in the methods of the present invention may be obtained from tissues such as, for example, bone marrow, umbilical cord blood, amniotic sac, amniotic fluid, placenta, skin, fat, muscle, vasculature, liver, pancreas, or peripheral blood, using methods that are well known in the art. Isolation of a population of mesenchymal stem cells may be achieved using monoclonal antibodies specific proteins expressed on the surface of MSC's. The monoclonal antibodies may be adhered to substrate to facilitate the separation of the bound cells. The methods that may be used to isolate MSC's suitable for use in the present invention may be chosen by one of ordinary skill in the art. Examples of such methods are taught in U.S. Pat. No. 6,087,113, U.S. Pat. No. 6,261,549, U.S. Pat. No. 5,914,262, U.S. Pat. No. 5,908,782, and US20040058412.

MSC's may be characterized, for example, by growth characteristics (e.g., population doubling capability, doubling time, passages to senescence), karyotype analysis (e.g., normal karyotype; maternal or neonatal lineage), flow cytometry (e.g., FACS analysis), immunohistochemistry and/or immunocytochemistry (e.g., for detection of epitopes), gene expression profiling (e.g., gene chip arrays; polymerase chain reaction (for example, reverse transcriptase PCR, real time PCR, and conventional PCR)), protein arrays, protein secretion-19 (e.g., by plasma clotting assay or analysis of PDC-conditioned medium, for example, by Enzyme Linked Immuno-Sorbent Assay (ELISA)), mixed lymphocyte reaction (e.g., as measure of stimulation of PBMCs), and/or other methods known in the art.

Mesenchymal stem cells suitable for use in the methods of the present invention may also include cells obtained from commercial sources, such as, for example human mesenchymal stem cells sold under the trade name POIETICS™ (Cat. No PT-2501, Cambrex). These mesenchymal stem cells are positive for the expression of the following markers: CD29, CD44, CD105 and CD166. The cells are negative for the expression of the markers CD14, CD34 and CD45.

Isolated MSC's, or tissue from which MSC's are obtained may be used to initiate, or seed, cell cultures. Isolated cells may be transferred to sterile tissue culture vessels, either uncoated or coated with extracellular matrix or ligands such as laminin, collagen (native, denatured or crosslinked), gelatin, fibronectin, and other extracellular matrix proteins. MSC's may be cultured in any culture medium capable of sustaining growth of the cells such as, for example, DMEM (high or low glucose), advanced DMEM, DMEM/MCDB 201, Eagle's basal medium, Ham's F10 medium (F10), Ham's F-12 medium (F12), Iscove's modified Dulbecco's-17 medium, Mesenchymal Stem Cell Growth Medium (MSCGM), DMEM/F12, RPMI 1640, and CELL-GRO-FREE. The culture medium may be supplemented with one or more components including, for example, fetal bovine serum (FBS); equine serum (ES); human serum (HS); beta-mercaptoethanol (BME or 2-ME), preferably about 0.001% (v/v); one or more growth factors, for example, platelet-derived growth factor (PDGF), epidermal growth factor (EGF), fibroblast growth factor (FGF), vascular endothelial growth factor (VEGF), insulin-like growth factor-1 (IGF-1), leukocyte inhibitory factor (LIF) and erythropoietin; amino acids, including L-valine; and one or more antibiotic and/or antimycotic agents to control microbial contamination, such as, for example, penicillin G. streptomycin sulfate, amphotericin B. gentamicin, and nystatin, either alone or in combination. The cells may be seeded in culture vessels at a density to allow cell growth.

Methods for the selection of the most appropriate culture medium, medium preparation, and cell culture techniques are well known in the art and are described in a variety of sources, including Doyle et al., (eds.), 1995, CELL & TISSUE CULTURE: LABORATORY PROCEDURES, John Wiley & Sons, Chichester; and Ho and Wang (eds.), 1991, ANIMAL CELL BIOREACTORS, Butterworth-Heinemann, Boston.

Use of Mesenchymal Stem Cells to treat Ophthalmic Disease.

In one aspect of the present invention, MSC's are used as a cell therapy for treating an ocular degenerative condition. Once transplanted into a target location in the eye, MSC's may provide trophic support for ocular cells in situ, or they may themselves differentiate into one or more phenotypes, or they may exert a beneficial effect in both of those fashions, among others.

MSC's may be administered alone (e.g., as substantially homogeneous populations) or as mixtures with other cells. MSC's may be administered in a pharmaceutical preparation, using conventional pharmaceutically acceptable carriers. Where MSC's are administered with other cells, they may be administered simultaneously or sequentially with the other cells (either before or after the other cells). Cells that may be administered in conjunction with MSC's include, but are not limited to, neurons, astrocytes, oligodendrocytes, neural progenitor cells, neural stem cells, ocular progenitor cells, retinal or corneal epithelial stem cells and/or other multipotent or pluripotent stem cells. The cells of different types may be mixed with the MSC's immediately or shortly prior to administration, or they may be co-cultured together for a period of time prior to administration.

The MSC's may be administered with at least one pharmaceutical agent, such as, for example, growth factors, trophic factors, conditioned medium, or other active agents, such as anti-inflammatory agents, anti apoptotic agents, antioxidants, neurotrophic factors or neuroregenerative or neuroprotective drugs as known in the art. When MSC's are administered with other agents, they may be administered together in a single pharmaceutical composition, or in separate pharmaceutical compositions, simultaneously or sequentially with the other agents (either before or after administration of the other agents).

Examples of other components that may be administered with mesenchymal stem cells include, but are not limited to: (1) other neuroprotective or neurobeneficial drugs; (2) selected extracellular matrix components, such as one or more types of collagen known in the art, and/or growth factors, platelet-rich plasma, and drugs (alternatively, the cells may be genetically engineered to express and produce growth factors); (3) anti-apoptotic agents (e.g., erythropoietin (EPO), EPO mimetibody, thrombopoietin, insulin-like growth factor (IGF)-I, IGF-II, hepatocyte growth factor, caspase inhibitors); (4) anti-inflammatory compounds (e.g., p38 MAP kinase inhibitors, TGF-beta inhibitors, stating, IL-6 and IL-1 inhibitors, PEMIROLAST, TRANILAST, REMICADE, SIROLIMUS, and non-steroidal anti-inflammatory drugs (NSAIDS) (such as-36 TEPOXALIN, TOLMETIN, and SUPROFEN); (5) immunosuppressive or immunomodulatory agents, such as calcineurin inhibitors, mTOR inhibitors, antiproliferatives, corticosteroids and various antibodies; (6) antioxidants such as probucol, vitamins C and E, conenzyme Q-10, glutathione, L-cysteine and N-acetylcysteine; and (6) local anesthetics, to name a few.

In one embodiment, MSC's may be administered as undifferentiated cells, i.e., as cultured in Growth Medium. Alternatively, MSC's may be administered following exposure in culture to conditions that stimulate differentiation toward a desired phenotype. The cells may be surgically implanted, injected or otherwise administered directly or indirectly to the site of ocular damage or distress. When cells are administered in semi-solid or solid devices, surgical implantation into a precise location in the body is typically a suitable means of administration. Liquid or fluid pharmaceutical compositions, however, may be administered to a more general location in the eye (e.g., topically or intra-ocularly).

Other embodiments encompass methods of treating ocular degenerative conditions by administering pharmaceutical compositions comprising MSC cellular components (e.g., cell lysates or components thereof) or products (e.g., trophic and other biological factors produced naturally by MSC's or through genetic modification, conditioned medium from MSC culture).

Again, these methods may further comprise administering other active agents, such as growth factors, neurotrophic factors or neuroregenerative or neuroprotective drugs as known in the art.

Dosage forms and regimes for administering MSC's or any of the other pharmaceutical compositions described herein are developed in accordance with good medical practice, taking into account the condition of the individual patient, e.g., nature and extent of the ocular degenerative condition, age, sex, body weight and general medical condition, and other factors known to medical practitioners. Thus, the effective amount of a pharmaceutical composition to be administered to a patient is determined by these considerations as known in the art.

It may be desirable or appropriate to pharmacologically immunosuppress a patient prior to initiating cell therapy. This may be accomplished through the use of systemic or local immunosuppressive agents, or it may be accomplished by delivering the cells in an encapsulated device. These and other means for reducing or eliminating an immune response to the transplanted cells are known in the art. As an alternative, MSC's may be genetically modified to reduce their immunogenicity.

According to another aspect of the invention, a method is provided for treating a patient having an ocular degenerative condition, which may comprise administering to the patient a preparation made from mesenchymal stem cells, in an amount effective to treat the ocular degenerative condition, wherein the preparation comprises a cell lysate of the MSC's, or a conditioned medium in which the MSC's were grown, or an extracellular matrix of the MSC's. The lysate may comprise at least one or all of the sub-cellular fractions of the MSC's, such as, for example the plasma membrane fraction. Methods of lysing cells are well known in the art and include various means of mechanical disruption, enzymatic disruption, or chemical disruption, or combinations thereof. Such cell lysates may be prepared from cells directly in their growth medium and thus containing secreted growth factors and the like, or may be prepared from cells washed free of medium in, for example, PBS or other solution. Washed cells may be resuspended at concentrations greater than the original population density if preferred. In one embodiment, whole cell lysates may be prepared, e.g., by disrupting cells without subsequent separation of cell fractions. In another embodiment, a cell membrane fraction is separated from a soluble fraction of the cells by routine methods known in the art, e.g., centrifugation, filtration, or similar methods.

Cell lysates or cell soluble fractions prepared from populations of MSC's may be used as is, further concentrated, by for example, ultrafiltration or lyophilization, or even dried, partially purified, combined with pharmaceutically-acceptable carriers or diluents as are known in the art, or combined with other compounds such as biologicals, for example pharmaceutically useful protein compositions. Cell lysates or fractions thereof may be used in vitro or in vivo, alone or for example, with autologous or allogenic live cells. The lysates, if introduced in vivo, may be introduced locally at a site of treatment, or remotely to provide, for example needed cellular growth factors to a patient.

In another aspect, the invention features a pharmaceutical composition comprising a pharmaceutically acceptable carrier and a preparation made from the mesenchymal stem cells, which may be a lysate of the MSC's, an extracellular matrix of the MSC's or a conditioned medium in which MSC's were grown. Kits for practicing this aspect of the invention are also provided. These may include the one or more of a pharmaceutically acceptable carrier or other agent or reagent, one or more of a cell lysate or fraction thereof, an extracellular matrix or a conditioned medium from the MSC's, and instructions for use of the kit components.

Pharmaceutical Formulations.

Pharmaceutical compositions of the invention may comprise postpartum cells MSC's, or components or products thereof, formulated with a pharmaceutically acceptable carrier or medium. Suitable pharmaceutically acceptable carriers include water, salt solution (such as Ringer's solution), alcohols, oils, gelatins, and carbohydrates, such as lactose, amylose, or starch, fatty acid esters, hydroxymethylcellulose, and polyvinyl pyrolidine. Such preparations may be sterilized, and if desired, mixed with auxiliary agents such as lubricants, preservatives, stabilizers, wetting agents, emulsifiers, salts for influencing osmotic pressure, buffers, and coloring. Typically, but not exclusively, pharmaceutical compositions comprising cellular components or products, but not live cells, are formulated as liquids. Pharmaceutical compositions comprising live MSC's are typically formulated as liquids, semisolids (e.g., gels) or solids (e.g., matrices, supports and the like, as appropriate for ophthalmic tissue engineering).

Pharmaceutical compositions may comprise auxiliary components as would be familiar to medicinal chemists or biologists. For example, they may contain antioxidants in ranges that vary depending on the kind of antioxidant used. Reasonable ranges for commonly used antioxidants are about 0.01% to about 0.15% weight by volume of EDTA, about 0.01% to about 2.0% weight volume of sodium sulfite, and about 0.01% to about 2.0% weight by volume of sodium metabisulfite. One skilled in the art may use a concentration of about 0.1% weight by volume for each of the above. Other representative compounds include mercaptopropionyl glycine, N-acetyl cysteine, beta-mercaptoethylamine, glutathione and similar species, although other anti-oxidant agents suitable for ocular administration, e.g. ascorbic acid and its salts or sulfite or sodium metabisulfite may also be employed.

A buffering agent may be used to maintain the pH of eye drop formulations in the range of about 4.0 to about 8.0; so as to minimize irritation of the eye. For direct intravitreal or intraocular injection, formulations should be at pH 7.2 to 7.5, alternatively at pH 7.3-7.4. The ophthalmologic compositions may also include tonicity agents suitable for administration to the eye. Among those suitable is sodium chloride to make formulations approximately isotonic with 0.9% saline solution.

In certain embodiments, pharmaceutical compositions are formulated with viscosity enhancing agents. Such agents can be, for example, hydroxyethylcellulose, hydroxypropylcellulose, methylcellulose, and polyvinylpyrrolidone. The pharmaceutical compositions may have co-solvents added if needed. Suitable co-solvents may include glycerin, polyethylene glycol (PEG), polysorbate, propylene glycol, and polyvinyl alcohol. Preservatives may also be included, such as, for example, benzalkonium chloride, benzethonium chloride, chlorobutanol, phenylmercuric acetate or nitrate, thimerosal, or methyl or propylparabens.

Formulations for injection may be designed for single-use administration and do not contain preservatives. Injectable solutions nay have isotonicity equivalent to 0.9% sodium chloride solution (osmolality of 290-300 milliosmoles). This may be attained by addition of sodium chloride or other co-solvents as listed above, or excipients such as buffering agents and antioxidants, as listed above.

The tissues of the anterior chamber of the eye are bathed by the aqueous humor, while the retina is under continuous exposure to the vitreous. These fluids/gels exist in a highly reduced state because they contains antioxidant compounds and enzymes. Therefore, it may be advantageous to include a reducing agent in the ophthalmologic compositions. Suitable reducing agents include N-acetylcysteine, ascorbic acid or a salt form, and sodium sulfite or metabisulfite, with ascorbic acid and/or N-acetylcysteine or glutathione being particularly suitable for injectable solutions.

Pharmaceutical compositions comprising cells, cell components or cell products may be delivered to the eye of a patient in one or more of several delivery modes known in the art. In one embodiment that may be suitable for use in some instances, the compositions are topically delivered to the eye in eye drops or washes. In another embodiment, the compositions may be delivered to various locations within the eye via periodic intraocular injection or by infusion in an irrigating solution such as BSS or BSS PLUS (Alcon USA, Fort Worth, Tex.). Alternatively, the compositions may be applied in other ophthalmologic dosage forms known to those skilled in the art, such as pre-formed or in situ-formed gels or liposomes, for example as disclosed in U.S. Pat. No. 5,718,922 to Herrero-Vanrell. In another embodiment, the composition may be delivered to or through the lens of an eye in need of treatment via a contact lens (e.g. Lidofilcon B. Bausch & Lomb CW79 or DELTACON (Deltafilcon A) or other object temporarily resident upon the surface of the eye. In other embodiments, supports such as a collagen corneal shield (e.g. BIO-COR dissolvable corneal shields, Summit Technology, Watertown, Mass.) may be employed.

The compositions may also be administered by infusion into the eyeball, either through a cannula from an osmotic pump (ALZET, Alza Corp., Palo Alto, Calif.) or by implantation of timed-release capsules (OCCUSENT) or biodegradable disks (OCULEX, OCUSERT). These routes of administration have the advantage of providing a continuous supply of the pharmaceutical composition to the eye. This may be an advantage for local delivery to the cornea, for example.

Pharmaceutical compositions comprising live cells in a semi-solid or solid carrier are typically formulated for surgical implantation at the site of ocular damage or distress. It will be appreciated that liquid compositions also may be administered by surgical procedures. In particular embodiments, semi-solid or solid pharmaceutical compositions may comprise semi permeable gels, lattices, cellular supports and the like, which may be non-biodegradable or biodegradable. For example, in certain embodiments, it may be desirable or appropriate to sequester the exogenous cells from their surroundings, yet enable the cells to secrete and deliver biological molecules to surrounding cells. In these embodiments, cells may be formulated as autonomous implants comprising living MSC's or cell population comprising MSC's surrounded by a non-degradable, selectively permeable barrier that physically separates the transplanted cells from host tissue. Such implants are sometimes referred to as "immunoprotective," as they have the capacity to prevent immune cells and macromolecules from killing the transplanted cells in the absence of pharmacologically induced immunosuppression (for a review of such devices and methods, see, e.g., P. A. Tresco et al., 2000, Adv. Drug Delivery Rev. 42: 3-27).

Supports.

In one aspect, the MSC's of the present invention may be incorporated into a support material prior to transplantation. Support materials suitable for use for purposes of the present invention include tissue templates, conduits, barriers, and reservoirs useful for tissue repair. In particular, synthetic and natural materials in the form of foams, sponges, gels, hydrogels, textiles, and nonwoven structures, which have been used in vitro and in vivo to reconstruct or regenerate biological tissue, as well as to deliver chemotactic agents for inducing tissue growth, are suitable for use in practicing the methods of the present invention. See, e.g., the materials disclosed in U.S. Pat. No. 5,770,417, U.S. Pat. No. 6,022,743, U.S. Pat. No. 5,567,612, U.S. Pat. No. 5,759,830, U.S. Pat. No. 6,626,950, U.S. Pat. No. 6,534,084, U.S. Pat. No. 6,306,424, U.S. Pat. No. 6,365,149, U.S. Pat. No. 6,599,323, U.S. Pat. No. 6,656, 488, and U.S. Pat. No. 6,333,029. Exemplary polymers suitable for use in the present invention are disclosed in U.S. Published Application 2004/0062753 A1 and U.S. Pat. No. 4,557,264.

To form a support incorporated with a pharmaceutical agent, the pharmaceutical agent may be mixed with the polymer solution prior to forming the support. Alternatively, a pharmaceutical agent may be coated onto a fabricated support, preferably in the presence of a pharmaceutical carrier. The pharmaceutical agent may be present as a liquid, a finely divided solid, or any other appropriate physical form. Alternatively, excipients may be added to the support to alter the release rate of the pharmaceutical agent. In an alternate embodiment, the support is incorporated with at least one pharmaceutical compound that is an anti-inflammatory compound, such as, for example compounds disclosed in U.S. Pat. No. 6,509,369.

In one embodiment, the support is incorporated with at least one pharmaceutical compound that is an anti-apoptotic compound, such as, for example, compounds disclosed in U.S. Pat. No. 6,793,945.

In another embodiment, the support is incorporated with at least one pharmaceutical compound that is an inhibitor of fibrosis, such as, for example, compounds disclosed in U.S. Pat. No. 6,331,298.

In a further embodiment, the support is incorporated with at least one pharmaceutical compound that is capable of enhancing angiogenesis, such as, for example, compounds disclosed in U.S. Published Application 2004/0220393 and U.S. Published Application 2004/0209901.

In still another embodiment, the support is incorporated with at least one pharmaceutical compound that is an immunosuppressive compound, such as, for example, compounds disclosed in U.S. Published Application 2004/0171623.

In a further embodiment, the support is incorporated with at least one pharmaceutical compound that is a growth factor, such as, for example, members of the TGF-β family, including TGF-β1, 2, and 3, bone morphogenic proteins (BMP-2, -3, -4, -5, -6, -7, -11, -12, and -13), fibroblast growth factors-1 and -2, platelet-derived growth factor-AA, and -BB, platelet rich plasma, insulin growth factor (IGF-I, II) growth differentiation factor (GDF-5, -6, -8, -10, -15), vascular endothelial cell-derived growth factor (VEGF), pleiotrophin, endothelin, among others. Other pharmaceutical compounds can include, for example, nicotinamide, hypoxia inducible factor 1-alpha, glucagon like peptide-I (GLP-1), GLP-1 and GLP-2 mimetibody, and II, Exendin-4, retinoic acid, parathyroid hormone, tenascin-C, tropoelastin, thrombin-derived peptides, cathelicidins, defensins, laminin, biological peptides containing cell- and heparin-binding domains of adhesive extracellular matrix proteins such as fibronectin and vitronectin, MAPK inhibitors, such as, for example, compounds disclosed in U.S. Published Application 2004/0209901 and U.S. Published Application 2004/0132729.

The incorporation of the cells of the present invention into a support may be achieved by the simple depositing of cells onto the support. Cells may enter into the support by simple diffusion (*J. Pediatr. Surg.* 23 (1 Pt 2): 3-9 (1988)). Several other approaches have been developed to enhance the efficiency of cell seeding. For example, spinner flasks have been used in seeding of chondrocytes onto polyglycolic acid supports (*Biotechnol. Prog.* 14(2): 193-202 (1998)). Another approach for seeding cells is the use of centrifugation, which yields minimum stress to the seeded cells and enhances seeding efficiency. For example, Yang et al. developed a cell seeding method (*J. Biomed. Mater. Res.* 55(3): 379-86 (2001)), referred to as Centrifugational Cell Immobilization (CCI).

Survival of transplanted cells in a living patient may be determined through the use of a variety of scanning techniques, e.g., computerized axial tomography (CAT or CT) scan, magnetic resonance imaging (MRI) or positron emission tomography (PET) scans.

Determination of transplant survival may also be done post mortem by removing the tissue and examining it visually or through a microscope. Alternatively, cells may be treated with stains that are specific for neural or ocular cells or products thereof, e.g., neurotransmitters. Transplanted cells may also be identified by prior incorporation of tracer dyes such as rhodamine- or fluorescein-labeled microspheres, fast blue, ferric microparticles, bisbenzamide or genetically introduced reporter gene products, such as beta-galactosidase or beta-glucuronidase.

Examining restoration of the ocular function that was damaged or diseased can assess functional integration of transplanted cells into ocular tissue of a subject. For example, effectiveness in the treatment of macular degeneration or other retinopathies may be determined by improvement of visual acuity and evaluation for abnormalities and grading of stereoscopic color fundus photographs (Age-Related Eye Disease Study Research Group, NEI, NIH, AREDS Report No. 8, 2001, Arch. Ophthalmol. 119:1417-1436).

The present invention is further illustrated, but not limited by, the following examples.

EXAMPLE

Use of Mesenchymal Stem Cells in the Treatment of Retinitis Pigmentosa

Royal College of Surgeon (RCS) rats are genetically predisposed to undergo significant visual loss caused by a primary dysfunction of retinal pigment epithelial (RPE) cells. Using this model, the efficacy of subretinal transplantation of mesenchymal stem cell populations to preserve photoreceptors in RCS rats was tested. In this degenerative model, rod function is lost within 30 to 60 days after birth. Loss of cone function usually follows within 3 months.

Preparation of MSC's for Transplantation.

Cultures of human adult MSC's (Cat. No. PT-2501, Cambrex) were expanded in vitro for a total of 6 passages. All cells were initially seeded at 5,000 cells/cm2 on non-coated T75 flasks in mesenchymal stem cell growth medium supplemented according to the manufacturer's instructions (Cambrex). For subsequent passages all cells were treated as follows. After trypsinization, viable cells were counted after trypan Blue staining. Briefly, 50 ml of cell suspension was combined with 50 ml of 0.04% w/v trypan Blue (Sigma, St. Louis Mo.) and the viable cell number, was estimated using a heamocytometer. Cells were trypsinized and washed three times in supplement free-DMEM:Low glucose medium (Invitrogen, Carlsbad, Calif.). Cultures of human MSCs cells at passage 6 were trypsinized and washed twice in Leibovitz's L-15 medium (Invitrogen, Carlsbad, Calif.), to remove serum components. For the transplantation procedure dystrophic RCS rats were anesthetized with xylazine-ketamine (1 mg/kg i.p. of the following mixture: 2.5 ml xylazine at 20 mg/ml, 5 ml ketamine at 100 mg/ml, and 0.5 ml distilled water) and their head secured by a nose bar. Cells devoid of serum were resuspended ($2 \times 10^4$ cells per injection) in 2 ml of Leibovitz, L-15 medium (Invitrogen, Carlsbad, Calif.) and transplanted using a fine glass pipette (internal diameter 75-150 mm) trans-scerally. Cells were delivered into the dorso-temporal subretinal space of anesthetized 3 week old dystrophic-pigmented RCS rats (total N=10/cell type).

Cells were injected unilaterally into the right eye, whilst the left eye was injected with carrier medium alone (Sham control; Leibovitz's L-15 medium). Viability of residual uninjected cells remained at greater than 95% as assessed by trypan blue exclusion at the completion of cell injections. After cell injections were performed animals were injected with dexamethasone (2 mg/kg) for 10 days post transplantation. For the duration of the study animals were maintained on oral cyclosporine A (210 mg/L of drinking water; resulting blood concentration: 250-300 mg/L) (Bedford Labs, Bedford, Ohio) from 2 days pre-transplantation until end of the study. Food and water were available ad libitum. Animals were sacrificed at 60 or 90 days postoperatively with the remainder of animals being sacrificed at earlier time-points for histological assessment of short-term changes associated with cell transplantation.

The ability of other cell types to treat the ocular degeneration observed in RCS rats was also tested. Cellular compositions were prepared from human umbilical-derived cells (cells disclosed in published U.S. Patent Application US2005/0054098), human placental-derived cells (cells disclosed in published U.S. Patent Application US2005/0058631) and fibroblasts. The cellular compositions were administered to parallel groups pf animals according to the methods described above.

Functional Assays.

Electroretinogram Recordings:

The electroretinogram (ERG) is a recording of electrical potentials (action potentials) that are generated within the retina (typically in response to a flash of light). It is recorded using two electrodes, with one electrode placed on or close to the cornea of the eye whilst the other is placed on the scalp. Following overnight dark adaptation, animals were prepared for ERG recording under dim red light, as described in Sauve et al, 2004. In brief, under anesthesia (with a mixture of 150 mg/kg i.p ketamine, and 10 mg/kg i.p. xylazine) the head was secured with a stereotaxic head holder and the body temperature monitored through a rectal thermometer and maintained at 38° C. using a homeothermic blanket. Pupils were dilated using equal parts of topical 2.5% phenylephrine and 1% tropicamide. Topical anesthesia with 0.75% bupivacaine was used to prevent any corneal reflexes and a drop of 0.9% saline was frequently applied on the cornea to prevent its dehydration and allow electrical contact with the recording electrode (gold wire loop). A 25-gauge needle inserted under the scalp, between the two eyes, served as the reference electrode. Amplification (at 1-1000 Hz bandpass, without notch filtering), stimulus presentation, and data acquisition were provided by the UTAS-3000 system from LKC Technologies (Gaithersburg, Md.).

A double flash protocol was used to determine the isolation of rod and cone responses (Nixon et al, 2001). A probe flash was presented 1 sec after a conditioning flash, using a specific feature of the UTAS-3000 system (LKC Technologies) with calibrated ganzfeld; assuring complete recharge of the stimulator. The role of the conditioning flash in this procedure was to transiently saturate rods so that they were rendered unresponsive to the probe flash. Response to the probe flash was taken as reflecting cone-driven activity a-wave). A rod-driven b-wave was obtained by subtracting the cone-driven response from the mixed response (obtained following presentation of a probe flash alone, i.e. not preceded by any conditioning flash).

For the quantification of dark-adapted b-waves, recordings consisted of single flash presentations (10 µsec duration), repeated 3 to 5 times to verify the response reliability and improve the signal-to-noise ratio, if required. Stimuli were presented at six increasing intensities in one log unit steps varying from −3.6 to 1.4 log candila/m2 in luminance. To minimize the potential bleaching of rods, inter-stimulus intervals were increased as the stimulus luminance was elevated from 10 sec at lowest stimulus intensity up to 2 minutes at highest stimulus intensity. The maximum b-wave amplitude was defined as that obtained from the flash intensity series, regardless of the stimulus intensity (Nusinowitz et al, 1999).

Animals that received umbilical cell injections (n=6) demonstrated improvement in all outcome measures tested at 60 days, a-wave (27±11) versus sham controls (0), mixed b-wave (117±67) versus sham controls (18±13), cone-b-wave (55±25) versus sham controls (28±11), and in rod contribution (49±16%) versus sham controls (6±7%). Furthermore, at 90 days improved responses were measured in 2 animals tested with measures being, a-wave (15±7) versus sham controls (0), mixed b-wave (37±15) versus sham controls (0), cone-b-wave (16±11) versus sham controls (7±5), and in rod contribution (58±39%) versus sham controls (0%). (FIG. 1). The response observed in these animals was much greater than that seen with un-treated or sham treated animals. MSC injections (n=5) at 58 days showed responsiveness to a-wave measurements (16.4±13.1) versus sham controls (14.6±12.5). Functional preservation of vision was demonstrated in mixed b-wave responsiveness (81.6±15.3) versus shams (54.4±24.5), and in isolated cone-b-wave responsiveness (134±68) versus shams (72.4±40.8), and in overall measures of rod contribution (41±16.8) versus shams (21±19.34). These results demonstrated demonstrate preservation of photoreceptor function at 60 days in these animals.

MSC injections (n=5) at 88 days in the same animals demonstrated significant preservation in all the ERG measures when compared to sham controls. Responsiveness to a-wave measurements (14.3±12.1) versus sham controls (0). Functional preservation of vision was demonstrated in mixed b-wave responsiveness (64.5±24) versus shams (0), and in isolated cone-b-wave responsiveness (32.6±22.7) versus shams (8±4), and in overall measures of rod contribution (47.5±29) versus shams (0). These results demonstrated improvement in visual responsiveness when compared to sham controls. Thus, the data clearly demonstrates that visual function is preserved in RCS animals that receive MSC injections vs sham controls, where vision is lost by 90 days.

Placental cell transplants (n=4) at 60 days showed no improvement in a-wave (20±20) versus sham controls (0), but showed minor improvement in mixed b-wave (81±72) versus sham controls (1.5±2), and good improvement in cone-b-wave (50±19) versus sham controls (7±7), and in rod contribution (30%) versus sham controls (0). These results indicated some improvement in visual responsiveness when compared to sham controls. This suggests that photoreceptor rescue was observed in these animals to a small extent (FIG. 1).

In contrast, animals receiving fibroblast transplantations showed no improvement in any of the parameters tested.

Functional Assessment:

Physiological retinal sensitivity testing was performed to demonstrate retinal response to dim light. In these tests animals were anesthetized with urethane at 1.25 g/kg i.p. Physiological assessment in these animals was tested post graft in animals at 90 days by recording multiunit extracellular activity in the superior colliculus to illumination of respective visual receptive fields (Lund et al, 2001). This procedure was repeated for 20 independent points (spaced 200 mm apart, with each step corresponding to approximately 10-150 displacements in the visual field), covering the visual field. Visual thresholds were measured as the increase in intensity over background and maintained at 0.02 candila/m2 (luminescence unit), required for activating units in the superficial 200 mm of the superior colliculus with a spot of light 30 in diameter. Response parameters were compared between transplanted and sham control eyes that received vehicle alone.

Figure 2:
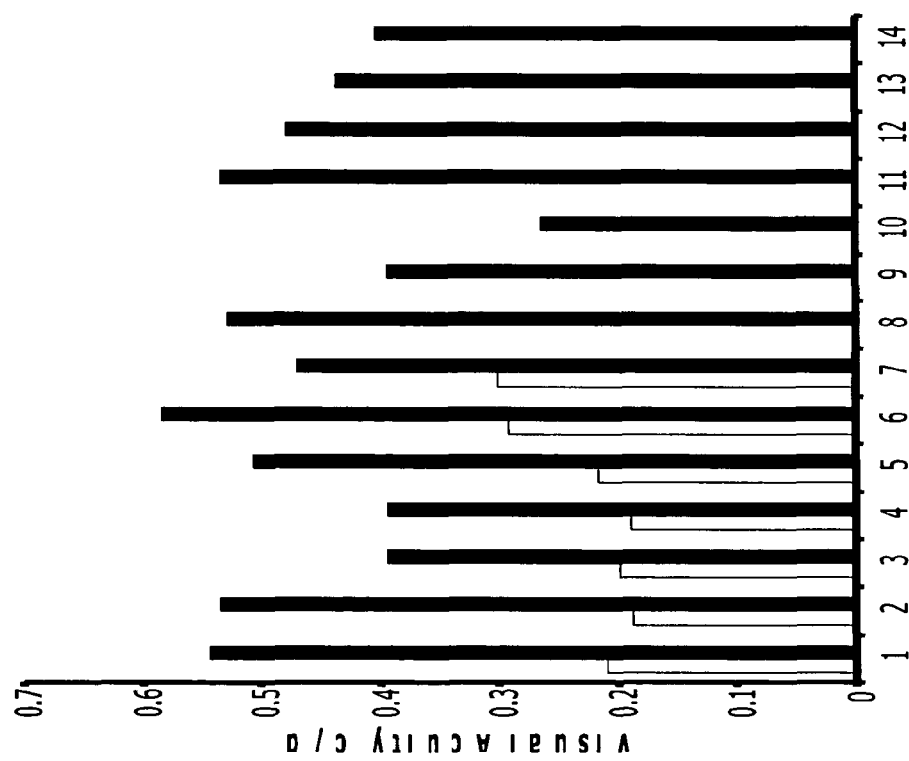
FIG. 2: Visual acuity of RCS rats receiving MSC's of the present invention. Data shown is the visual acuity of animals at 4 months of age (n=7), from sham operated rats (white bars), or MSC's of the present invention (Black bars).

Visual Acuity:

The grating acuity of RCS rats was tested after 3 and 4 months of age months. Normal animals demonstrate acuity of 0.5 cycles/degree at 3 months of age. After 3 months eyes injected with MSCs maintained an average acuity of 0.47 cycles/degree (n=14) in contrast to sham treated animals that retained an average acuity of 0.2 cycles/degree. Thus visual acuity was preserved in these animals 90 days post-graft. At 4 months of age MSC grafted animals maintained an average acuity of 0.36 cycles/degree (n=7), in contrast to sham treated animals that retained acuity at baseline levels (FIG. 2).

Figure 3:
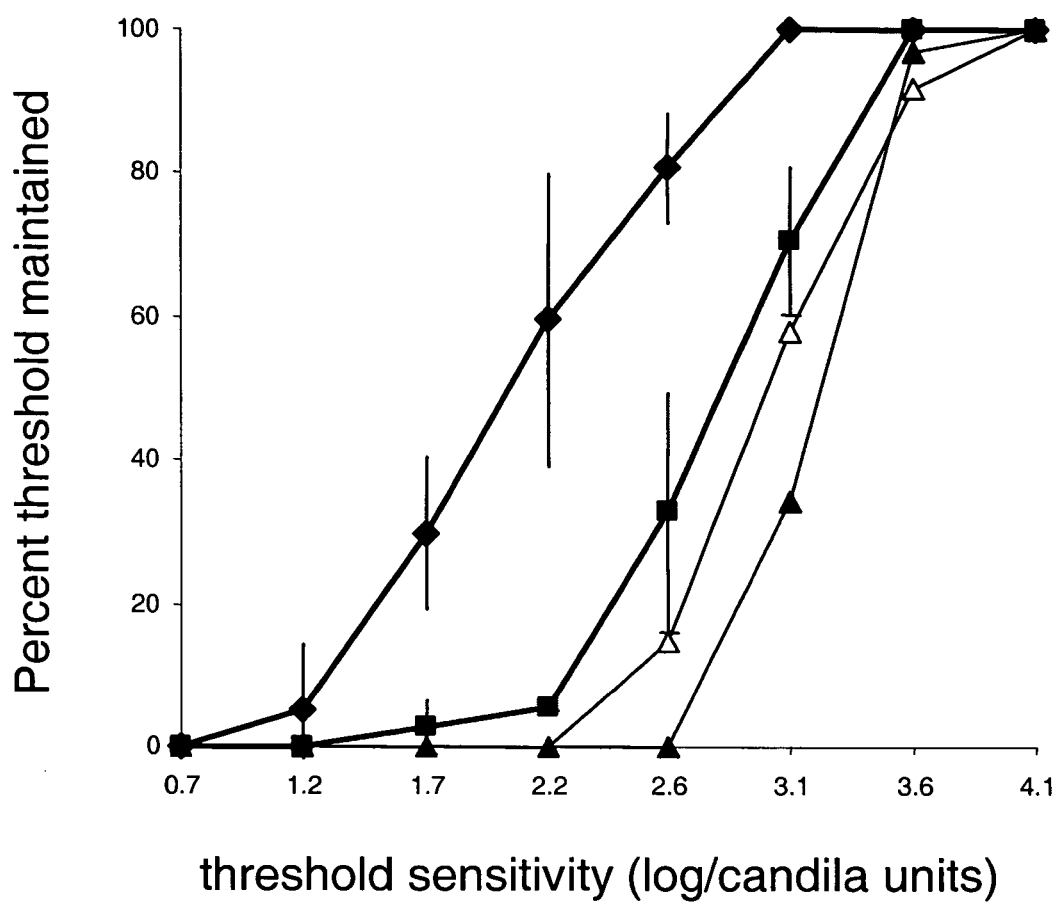
FIG. 3: Visual thresholds of RCS rats receiving MSC's of the present invention. Data shown is the visual acuity of animals at 4 months of age (n=7) that received grafts of MSC's in the left (Δ) or right (♦) eye. Data from contralateral sham operated eyes (left ▲: right ■) were included as controls.

Visual Thresholds:

Efficacy of transplants in preventing visual loss was monitored by assessment of electrophysiological responsiveness in 4 animals. The threshold sensitivity response to light was used to define the area of visual field rescue in sham-injected control eyes versus eyes transplanted with MSC's. In non-dystrophic rats, visual thresholds never exceeded 0.5 log candila/$m^2$ above background (FIG. 3). In non-operated dystrophic rats, the thresholds are usually in the magnitude of 4 log candila/$m^2$ units (Blakema and Drager, 1991). By contrast, in non-operated sham injected dystrophic rats, the thresholds were in the order of 2.9-4.9 log candila/$m^2$ units with an average threshold of 4.0 log candila/$m^2$ units, in some instances no recording could be attained (FIG. 3). Thus, the sham-injected rats showed some highly localized functional rescue in the temporal retina. However, the human MSC transplanted rats exhibited substantially greater levels of visual preservation with thresholds ranging from 0.8 to 2.1 log candila/m$^2$ units, with an average threshold of 1.3 log candila/m$^2$ units (FIG. 3). On average 60% of threshold responses were below 2.1 log candela units in MSC injected animals vs. 18% in sham injected controls.

Histology:

At the conclusion of the study, animals were sacrificed with an overdose of urethane (12.5 g/kg). The orientation of the eye was maintained by placing a 6.0 suture through the superior rectus muscle prior to enucleation. After making a corneal incision, the eyes were fixed with 2.5% parafomaldehyde, 2.5% glutaraldehyde, 0.01% picric acid in 0.1 M cacodylate buffer (pH7.4). After fixation, the cornea and lens were removed by cutting around the cilliary body. A small nick was made in the periphery of the dorsal retina prior to removal of the superior rectus to assist in maintaining orientation. The retinas were then post-fixed in 1% osmium tetroxide for 1 h. After dehydration through a series of alcohols to epoxypropane, the retinas were embedded in TAAB embedding resin (TAAB Laboratories, Aldemarston, UK). Semi-thin sections were stained with 1% toluidine Blue in 1% borate buffer and the ultra thin sections were contrasted with uranyl acetate and lead citrate.

For Nissl staining, sections were stained with 0.75% cresyl violet (Sigma, St. Louis, Mo.) after which they were dehydrated through graded alcohols at 70, 95 and 100% twice. They were then placed in xylene (Sigma, St. Louis, Mo.), rinsed with PBS (pH 7.4) (Invitrogen, Carlsbad, Calif.), coverslipped and mounted with DPX mountant (Sigma, St. Louis, Mo.).

Figure 4:
FIG. 4: A histological section of a retina from an animal receiving MSC's of the present invention. Tissue section was obtained from a grafted animal 100 days post procedure.

Histologicaly at the 90-100 day time point in MSC treated animals, anatomical rescue of host photoreceptors was clearly demonstrated (FIG. 4). The photoreceptors form a thick layer separated by a gap from the inner nuclear layer, made up of other retinal cells. The width of the outer layer in the sham control is at best a discontinuous single layer as opposed to around 3-5 cells thick in the grafted eye. In comparison to a normal animal this is marginally more than half the thickness of photoreceptor cell layers normally observed.

Publications cited throughout this document are hereby incorporated by reference in their entirety. Although the various aspects of the invention have been illustrated above by reference to examples and preferred embodiments, it will be appreciated that the scope of the invention is defined not by the foregoing description, but by the following claims properly construed under principles of patent law.

What is claimed is:

1. A method of treating a patient having retinitis pigmentosa, the method comprising administering to the patient mesenchymal stem cells in an amount effective to treat the retinitis pigmentosa, wherein the mesenchymal stem cells are characterized by the expression of CD105, and the lack of expression of CD34, and wherein the mesenchymal stem cells promote the survival of ocular cells, or the formation of photoreceptors from ocular cells in situ, but the mesenchymal stem cells do not form structures similar to the photoreceptor layer and do not express a photoreceptor-specific marker; or do not differentiate into photoreceptors themselves.

2. The method of claim 1, wherein the cells are administered to the surface of an eye.

3. The method of claim 1, wherein the cells are administered to the interior of an eye.

4. The method of claim 3, wherein the cells are administered through a cannula or from a device implanted in the patient's body within or in proximity to the eye.

5. The method of claim 3, wherein the cells are administered by implantation of a three dimensional matrix or support containing the cells.

6. The method of claim 3, wherein the method comprises administration of a pharmaceutical composition comprising the cells and a pharmaceutically acceptable carrier.

7. The method of claim 6, wherein the pharmaceutical composition is formulated for administration to the surface of an eye.

8. The method of claim 6, wherein the pharmaceutical composition is formulated for administration to the interior of an eye.

* * * * *